US008991138B2

(12) United States Patent
Yuyama et al.

(10) Patent No.: US 8,991,138 B2
(45) Date of Patent: Mar. 31, 2015

(54) MEDICINE DISPENSING DEVICE

(75) Inventors: Shoji Yuyama, Osaka (JP); Jyunichi Iwaya, Osaka (JP); Akifumi Tanaka, Osaka (JP)

(73) Assignee: Yuyama Mfg. Co., Ltd., Osaka (JP)

( * ) Notice: Subject to any disclaimer, the term of this patent is extended or adjusted under 35 U.S.C. 154(b) by 864 days.

(21) Appl. No.: 13/119,933

(22) PCT Filed: Sep. 17, 2009

(86) PCT No.: PCT/JP2009/004697
§ 371 (c)(1),
(2), (4) Date: Mar. 18, 2011

(87) PCT Pub. No.: WO2010/032475
PCT Pub. Date: Mar. 25, 2010

(65) Prior Publication Data
US 2011/0173926 A1 Jul. 21, 2011

(30) Foreign Application Priority Data

Sep. 19, 2008 (JP) ................................. 2008-241657
Feb. 5, 2009 (JP) ................................. 2009-025113
Sep. 16, 2009 (JP) ................................. 2009-214708

(51) Int. Cl.
*B65B 1/04* (2006.01)
*G07F 11/16* (2006.01)
(Continued)

(52) U.S. Cl.
CPC .............. *G07F 11/16* (2013.01); *G07F 11/165* (2013.01); *G07F 11/62* (2013.01); *G07F 17/0092* (2013.01)
USPC ................. 53/235; 53/237; 53/247; 700/216

(58) Field of Classification Search
USPC ........... 53/154, 493, 473, 167, 237, 247, 235; 221/92, 123, 124, 133; 700/216, 219, 700/244
See application file for complete search history.

(56) References Cited

U.S. PATENT DOCUMENTS 5,852,911 A * 12/1998 Yuyama et al. .................. 53/168
5,901,876 A * 5/1999 Yuyama et al. ............... 221/133
(Continued)

FOREIGN PATENT DOCUMENTS

CN 1655751 A 8/2003
CN 101262838 A 9/2006
(Continued)

*Primary Examiner* — Stephen F Gerrity
*Assistant Examiner* — Eyamindae Jallow
(74) *Attorney, Agent, or Firm* — Jones Day

(57) ABSTRACT

A medicine dispensing device including: a device body 3; a medicine containing unit 4 mounted in the device body 3 and including a plurality of medicine containers 9 configured to dispense medicines contained therein through a medicine ejecting portion; a medicine receiving unit 5 movably provided in the device body 3 and having at least two medicine receiving sections 26 that are moved to each of the medicine containers 9 of the medicine containing unit 4 to receive the medicine dispensed from the medicine ejecting portion and are moved to a discharging position to discharge the received medicines; a medicine collecting unit 6 having a plurality of medicine collecting sections 44 each collecting the medicines discharged from each of the medicine receiving sections 26 in the discharging position; and a control unit 7 configured to move each of the medicine receiving sections 26 to allow the medicine receiving section to receive the medicines dispensed from a corresponding medicine containing section and to discharge the medicines to a corresponding medicine collecting section 44 of the medicine collecting unit 6.

14 Claims, 30 Drawing Sheets

(51) Int. Cl.
*G07F 11/62* (2006.01)
*G07F 17/00* (2006.01)

(56) References Cited

U.S. PATENT DOCUMENTS

| | | | |
|---|---|---|---|
| 6,367,519 B2 * | 4/2002 | Thibiant et al. | 141/268 |
| 6,814,255 B2 * | 11/2004 | Liff et al. | 221/13 |
| 7,123,989 B2 * | 10/2006 | Pinney et al. | 700/237 |
| 7,228,198 B2 * | 6/2007 | Vollm et al. | 700/235 |
| 7,228,200 B2 * | 6/2007 | Baker et al. | 700/236 |
| 7,434,704 B2 | 10/2008 | Yuyama et al. | |
| 7,451,583 B2 * | 11/2008 | Kim | 53/154 |
| 7,721,508 B2 * | 5/2010 | Yuyama et al. | 53/249 |
| 7,787,986 B2 * | 8/2010 | Pinney et al. | 700/232 |
| 8,038,016 B2 * | 10/2011 | Yuyama et al. | 211/59.3 |
| 8,230,662 B2 * | 7/2012 | Boutin | 53/55 |
| 8,234,838 B2 * | 8/2012 | Yasunaga et al. | 53/55 |
| 8,281,553 B2 * | 10/2012 | Kim | 53/131.2 |
| 8,365,950 B2 * | 2/2013 | Yuyama et al. | 221/123 |
| 8,490,369 B2 * | 7/2013 | Foucher et al. | 53/493 |
| 2002/0092275 A1 * | 7/2002 | Kim | 53/493 |
| 2003/0029882 A1 | 2/2003 | Yuyama et al. | |
| 2003/0089085 A1 | 5/2003 | Shigeyama et al. | |
| 2005/0021173 A1 * | 1/2005 | Pinney et al. | 700/231 |
| 2006/0113314 A1 * | 6/2006 | Yuyama et al. | 221/222 |
| 2007/0221680 A1 * | 9/2007 | Yuyama | 221/124 |
| 2009/0114672 A1 * | 5/2009 | Schifman et al. | 221/133 |
| 2009/0289079 A1 * | 11/2009 | Yuyama | 221/133 |
| 2010/0147868 A1 | 6/2010 | Yuyama et al. | |

FOREIGN PATENT DOCUMENTS

| | | |
|---|---|---|
| EP | 1929991 A1 | 9/2006 |
| JP | 2003-230619 | 8/2003 |
| JP | 2007-117708 | 5/2007 |
| JP | 2007117708 A * | 5/2007 |
| WO | WO 01/68484 A1 | 9/2001 |
| WO | WO 2004/012647 A1 | 2/2004 |

\* cited by examiner (a)

(b)

(c)

(d)

(e)

(f)

(g)

(h)

(i)

(a)

(b)

(c)

(d)

AMPOULE DISPENSING OPERATION

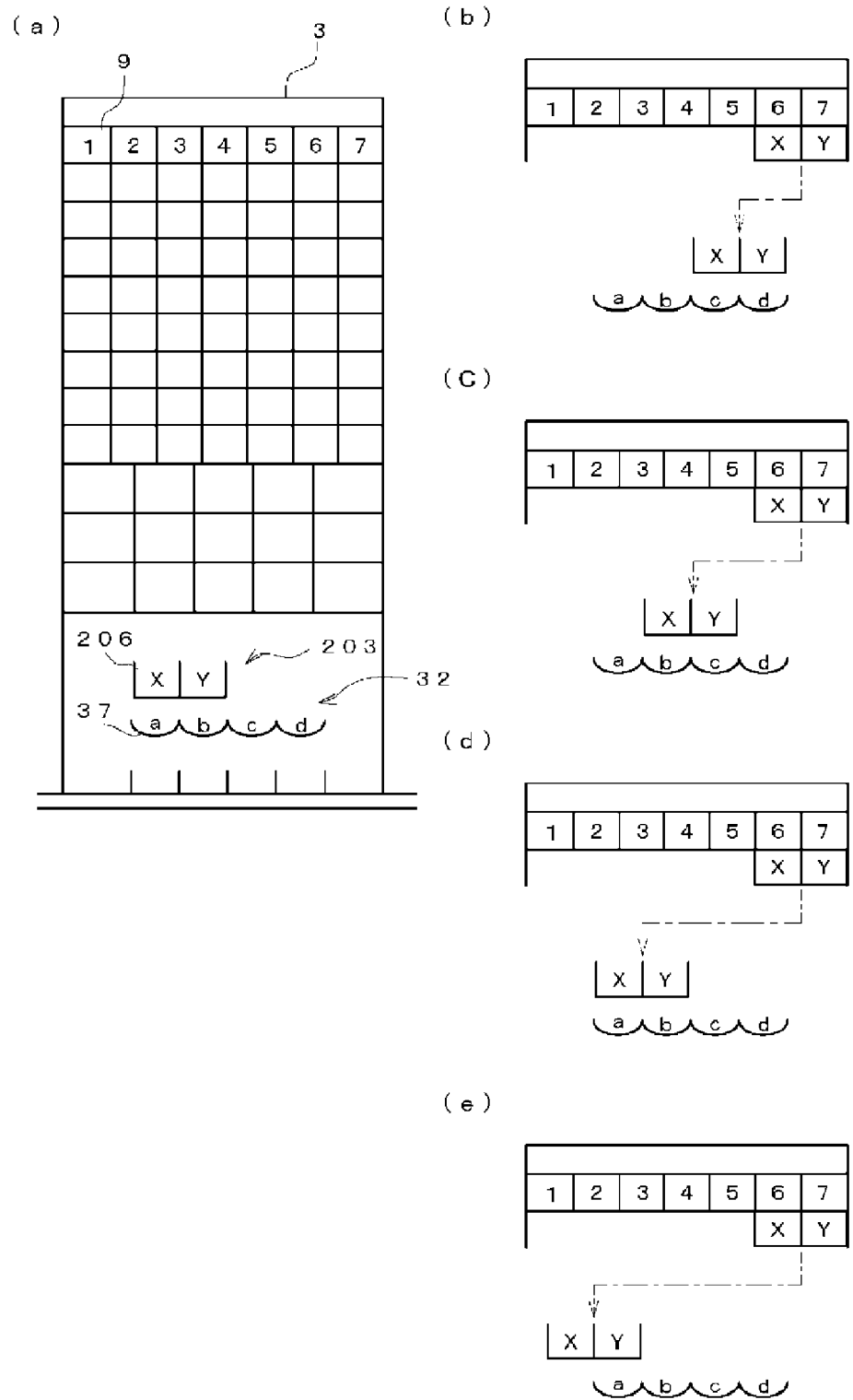

MEDICINE DISPENSING DEVICE

CROSS-REFERENCE TO RELATED APPLICATIONS

This application is a national-stage filing under 35 U.S.C. §371 of International Patent Application No. PCT/JP2009/004697, filed Sep. 17, 2009, the entire contents of which are incorporated by reference herein, which claims the benefit of the following applications, the entire contents of each of which are incorporated by reference herein:
Japanese Patent Application No. 2008-241657, filed Sep. 19, 2008;
Japanese Patent Application No. 2009-025113, filed Feb. 5, 2009; and
Japanese Patent Application No. 2009-214708, filed Sep. 16, 2009.

TECHNICAL FIELD

The present invention relates to a medicine dispensing device.

BACKGROUND OF THE INVENTION

There is known in the art a medicine dispensing device configured to arrange cassettes containing a plurality of ampoules in a device body in a matrix arrangement and to collect ampoules for four prescriptions together by means of four ampoule storing chambers provided in an ampoule collection section and then to dispense the same to a medicine collecting container (see, e.g., Patent Document 1).
Patent Document 1: Japanese Laid-Open Patent Application No. 2007-117708

SUMMARY OF THE INVENTION

However, when the ampoules are collected from the cassettes in the above-mentioned prior art medicine dispensing device, each ampoule containing chamber must be moved to a collection-permissible position through the rotation of an ampoule containing drum. This takes too much time to perform collection. Further, the medicine dispensing device is configured to dispense the ampoules collected in each ampoule storing chamber to each receiving chamber partitioned in a tray and thus cannot reduce time spent for dispensing. Recently, there has been a great demand for prompter medicine dispensing task. However, the aforesaid construction cannot sufficiently cope with such a demand.

Thus, it is an object of the present invention to provide a medicine dispensing device that can more rapidly collect medicines from a medicine containing unit and dispense medicines to medicine collecting unit.

As measures for achieving the foregoing object, the present invention provides a medicine dispensing device including the following: a device body; a medicine containing unit mounted in the device body, the medicine containing unit including a plurality of medicine containers configured to dispense medicines contained therein through a medicine ejecting portion; a medicine receiving unit movably provided in the device body, the medicine receiving unit having at least two medicine receiving sections that are moved to each of the medicine containers of the medicine containing unit to receive the medicines dispensed from the medicine ejecting portion and are moved to a discharging position to discharge the received medicines; a medicine collecting unit having a plurality of medicine collecting sections, each of the medicine collecting sections collecting the medicines discharged from each of the medicine receiving sections in the discharging position; and a control unit configured to move each of the medicine receiving sections based on a prescription data to allow the medicine receiving section to receive the medicines dispensed from the medicine container containing corresponding medicines and to concurrently discharge the medicines to the corresponding medicine collecting section of the medicine collecting unit.

According to such construction, a predetermined number of medicines can be dispensed from each of the medicine containers containing the corresponding medicine through the movement of the at least two medicine receiving sections. Accordingly, medicines can be dispensed to the medicine receiving sections in a short time. Further, the medicine dispensed to each of the medicine receiving sections can be discharged to the medicine collecting section through the movement of each of the medicine receiving sections to the corresponding medicine collecting section of the medicine collecting unit. Accordingly, a series of dispensing processes can be reliably and rapidly performed.

The medicine containing unit may be configured to arrange the medicine ejecting portions along any reference plane in the device body. The medicine receiving unit may include a supporting member supporting the medicine receiving sections such that each of the medicine receiving sections is movable upwardly, downwardly leftward and rightward along the reference plane.

The medicine receiving unit may include the medicine receiving container comprising two medicine receiving sections arranged horizontally side by side. The medicine receiving container may be horizontally and reciprocably provided such that each of the medicine receiving sections is positioned with respect to the medicine container wherein medicines are dispensed from the medicine ejecting portion.

According to such construction, when continuously dispensing medicines from the same medicine container, medicines can be simply received in each of the medicine receiving sections only by moving the medicine receiving sections arranged side by side. Accordingly, the medicines can be dispensed at high speed. Further, if the medicine receiving sections arranged side by side are moved to the medicine collecting unit and each medicine receiving section is positioned to each medicine collecting section, then dispensing medicines to the medicine collecting unit can be also performed promptly.

The medicine receiving unit may include four medicine receiving sections arranged horizontally side by side. The medicine receiving sections located at either end may be relatively moved upwardly or downwardly with respect to the medicine receiving sections located in two central places. Then, they may be moved toward one another to align with respect thereto.

The medicine receiving unit may include two medicine receiving containers each comprising two medicine receiving sections arranged horizontally side by side. Each of the medicine receiving sections of each of the medicine receiving containers may be changeable in upward, downward and leftward and rightward relative positions.

According to such construction including the four medicine receiving sections, all the medicines for one day prescription can be received in each medicine receiving section and further can be dispensed to each medicine collecting section of the medicine collecting unit at a time. Thus, a more efficient medicine dispensing operation can be achieved.

The medicine dispensing device may further comprise a medicine storing member having a plurality of medicine storing sections, each of the medicine storing sections temporarily storing the medicine received in each of the medicine receiving sections of the medicine receiving unit before the medicine received in each of the medicine receiving sections is discharged to each of the medicine collecting sections.

According to such construction, corresponding medicines can be dispensed from the medicine containers of the medicine containing unit based on the next prescription data before the next medicine collecting unit is ready. Thus, the dispensing operation can be performed at higher speed.

Preferably, the medicine may be longitudinally elongated. The medicine collecting unit may be configured such that the medicine collecting sections longitudinally elongated are arranged side by side in a direction orthogonal to a longitudinal direction thereof. The medicine dispensing device may further comprise an orientation changer between the medicine receiving unit and the medicine collecting unit, the orientation changer being pivotable between a receipt position where the medicine is received from the medicine receiving section of the medicine receiving unit and a delivery position where a longitudinal direction of the medicine is in accord with the longitudinal direction of the medicine collecting section.

According to such construction, when dispensing longitudinally elongated medicines, the orientation changer can accord the longitudinal direction of the medicine with the longitudinal direction of the orientation changer of the medicine collecting unit. Thus, medicines can be dispensed simply and reliably to each of the medicine collecting sections.

Preferably, at least two orientation changers among the orientation changers may be configured such that at least one begins to pivot from the receipt position to the delivery position and thereafter the other begins to pivot from the receipt position to the delivery position.

The reason for different time in beginning pivoting of the orientation changers is that the orientation changers located closely can be pivoted without any interference therebetween. Accordingly, if the orientation changers are spaced apart from each other, then the orientation changers may begin to pivot at the same time.

According to such configuration, the two orientation changers, even if disposed closely to each other, can smoothly change the orientation without any interference with each other, thus achieving compactness of the entire device.

Preferably, the plurality of the medicine storing sections of the medicine storing member may be configured to be lifted and lowered integrally and each of the medicine storing sections may be supported so as to be lifted and lowered independently.

According to such configuration, since a plurality of the medicine storing sections are lifted and lowered integrally, medicines can be dispensed to each of the medicine collecting sections of the medicine collecting unit. Further, when the medicine storing member is in abutment with the dispensed medicines, each medicine storing section is lifted independently, thus preventing the medicines from being damaged.

Preferably, the medicine contained in the medicine container may be an ampoule. The medicine containing unit may include a dispensing member dispensing the ampoule in a longitudinal direction of the ampoule one at a time. The medicine receiving unit may include: a receiving rotator supporting the dispensed medicine and transferring the supported medicine downwardly through rotation; and a bottom plate supporting the medicine transferred downwardly through the rotation of the receiving rotator and pivoting to discharge the medicine downwardly.

According to such construction, even if the medicine is an ampoule prone to sustain damages and the ampoule is dispensed in its longitudinal direction, the medicine receiving unit can smoothly receive the ampoule. That is, the ampoule supported by the receiving rotator can be transferred downwardly without impact thereon along with the rotation of the receiving rotator and thus can be supported on the bottom plate. Accordingly, the ampoule can be supported without any damage so that it can be discharged.

Preferably, the receiving rotator may include a receiving groove portion of U-shaped cross section. The receiving groove portion may be formed to be gradually downwardly inclined toward a direction of ejecting the medicine from the medicine container when the receiving rotator is in a normal position. Further, the receiving groove portion may include a buffer means buffering an impact exerted to the ampoule transferred.

According to such construction, the ampoule dispensed from the medicine container can be smoothly moved to the receiving groove portion of the receiving rotator. Thus, it is possible to sufficiently reduce the impact exerted to the ampoule to prevent the ampoule from sustaining damages.

Preferably, the receiving rotator may be rotatably supported on one side opposite the medicine container and open the receiving groove portion toward an end surface of the medicine container in the normal position.

According to such construction, the medicine container has a sufficient opening. Thus, the ampoule dispensed from the medicine container can be smoothly introduced to the receiving groove portion.

Preferably, the medicine receiving unit may include a partition plate, which is disposed along a rotation direction of the receiving rotator and guides the ampoule supported in the receiving groove portion until the ampoule is discharged to the bottom plate.

According to such construction, as the receiving rotator rotates, the ampoule supported on the receiving groove portion is guided by the partition plate and can be smoothly transferred to the bottom plate.

Preferably, the medicine receiving unit may include a plurality of receiving sections arranged horizontally side by side. The medicine receiving unit may be configured to be movable within a range wherein the medicine receiving unit does not protrude leftward and rightward in a frontal range of the medicine containers arranged upwardly, downwardly leftward and rightward.

According to such construction, the medicine receiving unit does not protrude laterally beyond the frontal area of the medicine containers. Thus, it is possible to compactly construct the entire device.

According to the present invention, the medicines dispensed from the medicine containing unit are received through the movement of the at least two medicine receiving sections and are then concurrently discharged to the medicine collecting unit. This allows for an accurate and high-speed process.

BRIEF DESCRIPTION OF THE DRAWINGS

FIG. 30 illustrates operations of dispensing medicines from the medicine containers in right-hand columns using the medicine receiving unit shown in FIG. 26.

DESCRIPTION OF REFERENCE NUMERAL

Figure 1:
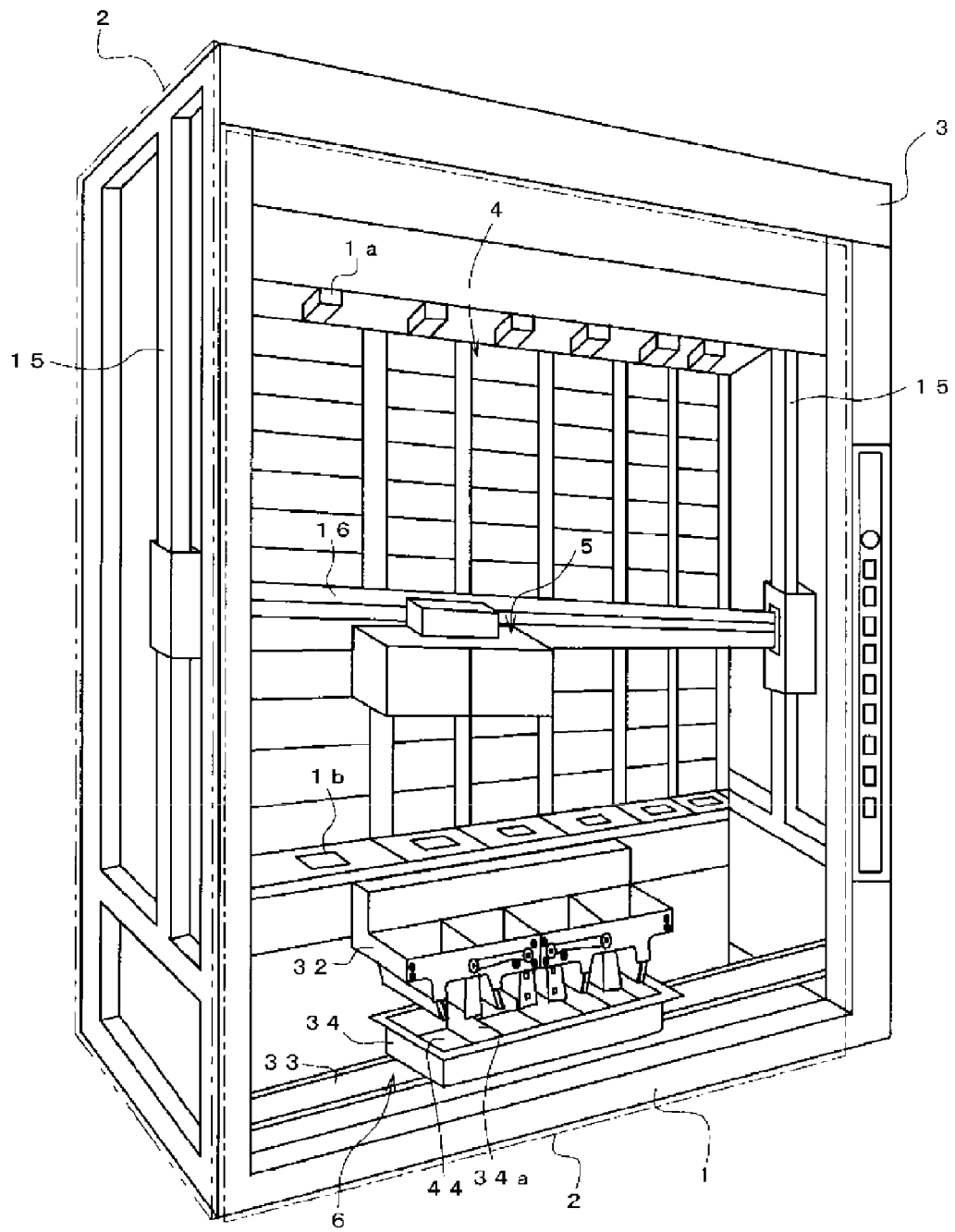
FIG. 1 is a perspective view showing a medicine dispensing device in accordance with one embodiment.

1 . . . Frame Body, 2 . . . External Panel, 3 . . . Device Body, 4 . . . Medicine Containing Unit, 5 . . . Medicine Receiving Unit, 6 . . . Medicine Collecting Unit, 7 . . . Control Unit, 8 . . . Cassette Containing Portion, 9 . . . Cassette (Medicine Container), 10 . . . Partition Wall, 11 . . . Horizontal Shelf, 12 . . . Ampoule, 13 . . . Rotor, 14 . . . Rod, 15 . . . Vertical Rail, 16 . . . Horizontal Rail, 17 . . . Slide Base, 18 . . . Projecting Unit, 19 . . . Medicine Receiving Container, 20 . . . Projecting Base, 21 . . . Projecting Motor, 22 . . . Projecting Pin, 23 . . . Front Plate, 24 . . . Side Plate, 25 . . . Midway Plate, 26 . . . Medicine Receiving Section, 27 . . . Bottom Plate, 31 . . . Elastic Sheet, 32 . . . Medicine Storing Member, 33 . . . Conveying Member, 34 . . . Medicine Collecting Container, 35 . . . Supporter, 36 . . . Body Portion, 37 . . . Medicine Storing Section, 38 . . . First Inclined Plate, 39 . . . Second Inclined Plate, 40 . . . Brush, 41 . . . First Inclined Section, 42 . . . Second Inclined Section, 43 . . . Elastic Sheet, 44 . . . Medicine Collecting Section, 45 . . . Projecting Unit, 46 . . . Top Plate, 47 . . . Side Plate, 48 . . . Partition plate, 49 . . . Frontal Plate, 50 . . . Projecting Unit, 51 . . . Vertical Drive Mechanism, 52 . . . First Slider, 53 . . . Second Slider, 54 . . . Medicine Receiving Container, 55 . . . Medicine Receiving Section, 56 . . . Frame, 57 . . . Bottom Plate, 58 . . . Medicine Receiving Section, 61 . . . Orientation changing Container, 62 . . . Spindle, 63 . . . Support plate, 64 . . . First Cam, 65 . . . Second Cam, 66 . . . Driven Gear, 67 . . . Drive Gear, 68 . . . Motor, 69 . . . First Arm Portion, 70 . . . Second Arm Portion, 71 . . . Cutout Groove, 72 . . . First Circular Arc Surface, 73 . . . Spindle, 74 . . . Larger-diameter Portion, 75 . . . Smaller-diameter Portion, 76 . . . Second Circular Arc Surface, 77 . . . Protrusion, 78 . . . Larger-diameter Gear, 81 . . . Back Portion, 82 . . . Guide Piece, 83 . . . Guide Shaft, 84 . . . First Support block, 85 . . . Second Support block, 86 . . . Slide Shaft, 87 . . . Coil Spring, 88 . . . Motor, 89 . . . Drive Gear, 90 . . . Driven Gear, 91 . . . Pulley, 92 . . . Belt, 93, 94 . . . Pulley, 95 . . . Belt, 96a . . . Gear, 97 . . . First Bottom Plate, 98 . . . Second Bottom Plate, 100 . . . Pulley, 101 . . . Belt, 102 . . . Motor, 103 . . . Connection Piece, 110 . . . Pulley, 111 . . . Belt, 112 . . . Spindle, 113 . . . Motor, 114 . . . Connection Portion, 120 . . . Motor, 121 . . . Pulley, 122 . . . Belt, 200 . . . Dispensing Member, 201 . . . Guide Passage, 202 . . . Rotor, 203 . . . Medicine Receiving Unit, 204 . . . Frame Body, 204a . . . Frontal Plate, 205 . . . Partition plate, 205a . . . Curved Surface, 206 . . . Receiving section, 207 . . . Receiving rotator, 207a . . . Spindle, 208 . . . Bottom Plate, 209 . . . Receiving groove Portion, 210 . . . Driven Gear, 211 . . . Motor, 212 . . . Drive Gear, 213 . . . Intermediate Gear, 214 . . . Guide Wall

DETAILED DESCRIPTION OF THE INVENTION

Embodiments of the present invention will be described with reference to the accompanying drawings. In the below description, the types, combinations, shapes, relative arrangement, etc. of elements or components are not intended to limit the scope of the present invention as described as such, unless specifically described. Further, where necessary, the terms (e.g., "upper," "lower," "front," "rear," "one end," "opposite end," etc.) are appropriately used herein for indicating a particular direction or position. However, those terms used herein are for easy understanding of the present invention with reference to the drawings and are not intended to limit the scope of the present invention on their meanings.

1. General Configuration

FIG. 1 shows a medicine dispensing device in accordance with one embodiment. The medicine dispensing device is constructed so that a medicine containing unit 4, a medicine receiving unit 5, a medicine collecting unit 6 and a control unit 7 (see FIG. 7) are provided in a device body 3 of general rectangular parallelepiped shape including a frame body 1 and external panels 2 mounted to the frame body.

1-1. Medicine Containing Unit 4

Figure 2:
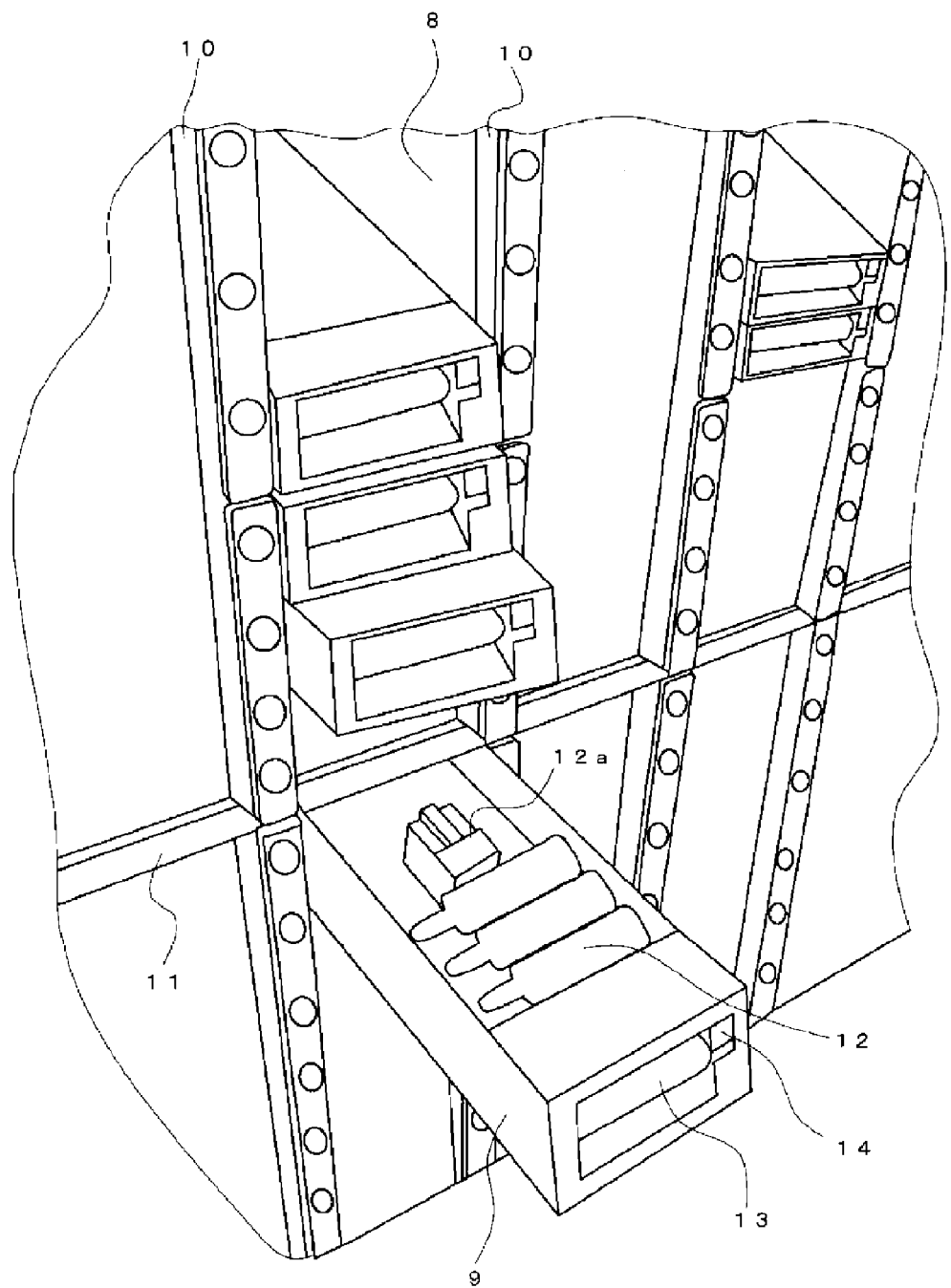
FIG. 2 is an enlarged fragmentary perspective view showing that a cassette is drawn out in FIG. 1.

As shown in FIG. 2, the medicine containing unit 4 includes a cassette containing portion 8 and a plurality of cassettes 9 (medicine containing portion) to be attached to and detached from the cassette containing portion. The cassette containing portion 8 includes a longitudinally elongated space formed by partitioning an interior of the device body 3 at predetermined intervals in a horizontal direction with a plurality of partition walls 10 and further partitioning the same half in a vertical direction with a horizontal shelf 11. Opposed surfaces of the partition wall 10 are constructed such that a plurality of the cassettes 9 are detachably arranged vertically one above another (not shown in detail).

The cassettes 9 contain a plurality of medicines according to their types. The cassettes are different from one another in terms of a width dimension, a height dimension and, on some occasions, a length (depth) dimension. In this embodiment, the cassette 9 contains ampoules 12 (the medicine) of general cylindrical shape as the ampoules are arranged in a diametrical direction. A constant force spring 12a biases the ampoules 12 toward a medicine dispensing side, thus arranging the ampoules one behind another without any gap therebetween. Further, as a rotor 13 constituting a medicine dispensing portion is rotated, the ampoules are dispensed one at a time. The rotor 13 includes a concave portion (not shown) conforming to an outer periphery of the ampoule 12. Rotation of the rotor 13 is made by pushing in a rod 14 biased in a projection direction and rotating a pinion provided in a rotating shaft of the rotor 13 through a rack formed in the rod 14. Further, each of the cassettes 9 is positioned such that an ejection position from the rotor 13 becomes parallel to any reference plane (a plane parallel to a front plane of the device body 1). Preferably, the cassette 9 has cutout portions (not shown) at upper and lower edges near the rotor 13, respectively. An optical sensor 1a and a reflector 1b provided above and below in each column of the device body 1 detect whether the ampoule is dispensed to the cutout portion. This allows for reliable detection since when the rotor 13 is rotated and the ampoule 12 is dispensed thereby, the ampoule 12 intercepts an irradiated light in the cutout portion and the sensor 1a does not receive the irradiated light. Further, if the sensor 1a remains in a light reception state even though the ampoule is yet dispensed by the rotation of the rotor 13, a projecting operation (this will be described below) is repeated in order to rotate the rotor 13. If the sensor 1a still remains in the light reception state, then error may be notified. Since the absence or presence of the ampoule 12 is detected using the cutout portion formed in the cassette 9, erroneous detection that may be caused when using fingers or the medicine receiving unit 5 does not occur. Furthermore, the sensor 1a and the reflector 1b may detect that the cassette 9 is inserted or drawn out.

1-2. Medicine Receiving Unit 5

The medicine receiving unit 5 includes: a horizontal rail 16 attached to the frame body 1 (a pair of vertical rails 15 located left and right) on the front of the device body 3 so as to be upwardly and downwardly (vertically) reciprocable; and a slide base 17 attached to the horizontal rail 16 so as to be reciprocable leftward and rightward (horizontally). A projecting unit 18 and a medicine receiving container 19 are provided in the slide base 17.

The projecting unit 18 is constructed such that a projecting motor 21 and a projecting pin 22 is provided in a projecting base 20. The projecting base 20 has an inverted U shape and the projecting pin is provided in one end of the projecting base. The projecting pin 22 is reciprocated by the projecting motor 21 via a pinion and a rack (not shown) and pushes in the rod 14 provided in the medicine containing unit 4 to allow the ampoule to be dispensed one at a time.

Figure 3:
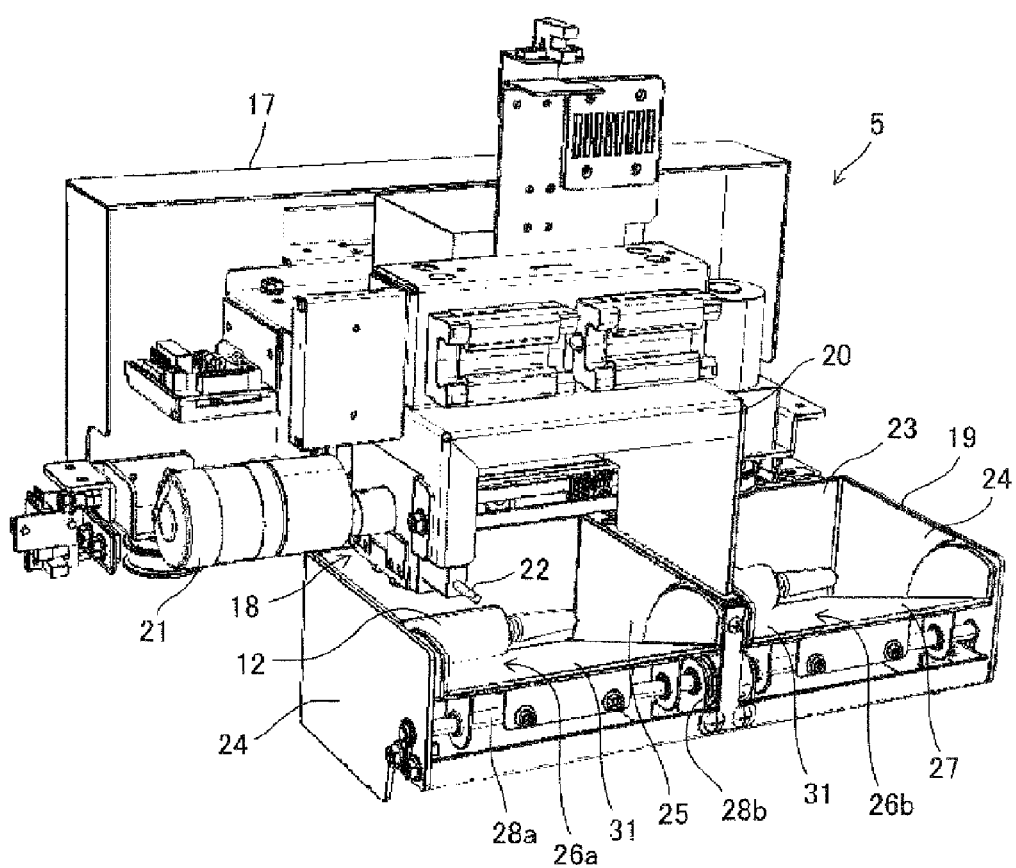
FIG. 3 is a perspective view showing a medicine receiving unit shown in FIG. 1.
Figure 4:
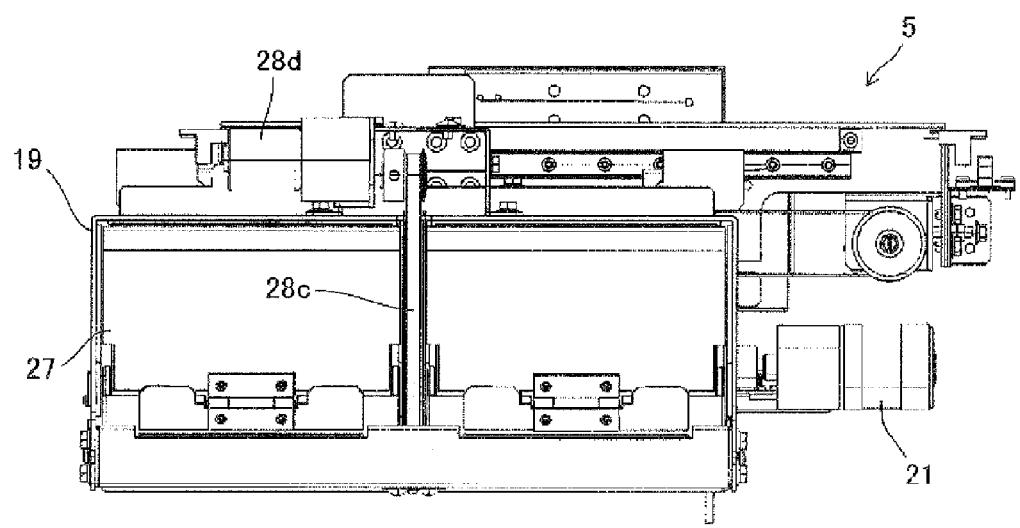
FIG. 4 is a bottom view of FIG. 3.

As shown in FIGS. 3 and 4, the medicine receiving container 19 is constructed such that side plates 24 and a midway plate 25 are integrated with both ends and a midway portion of a frontal plate 23, respectively, and bottom plates 27 are disposed at bottom sides of two enclosed sections (a first medicine receiving section 26a and a second medicine receiving section 26b). As shown in FIG. 3, elastic sheets 31 are disposed on the bottom plates 27. The bottom plates 27 are pivoted about the aforesaid spindle 28a. When the bottom side is closed, the bottom plates are gradually downwardly inclined toward the front plate 23. Thus, the ampoules 12 dispensed from the cassette 9 are smoothly received in each of the medicine receiving sections 26a, 26b. Further, a power from a motor 28d provided in front of the front plate 23 is transmitted to each bottom plate 27 via a belt 28c wound around a pulley 28b fixed to the spindle 28a, thus synchronously pivoting the bottom plates to open and close the bottom side. Further, the medicine receiving container 19 is moved horizontally relative to the slide base 17 to position each of the medicine receiving sections 26a, 26b with respect to the cassette 9, that is, the projecting base 20 of the projecting unit 28.

1-3. Medicine Collecting Unit 6

The medicine collecting unit 6 includes a medicine storing member 32 and a medicine collecting container 34 located beneath the medicine storing member and conveyed by a conveying member 33.

Figure 5:
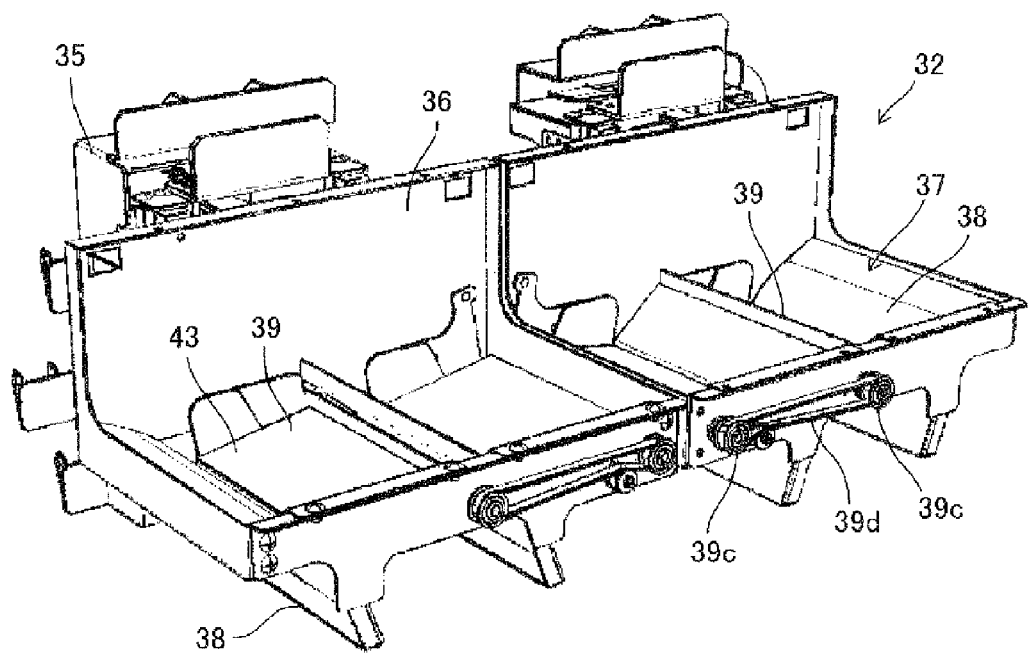
FIG. 5 is an upper perspective view of a medicine storing member shown in FIG. 1.
Figure 6:
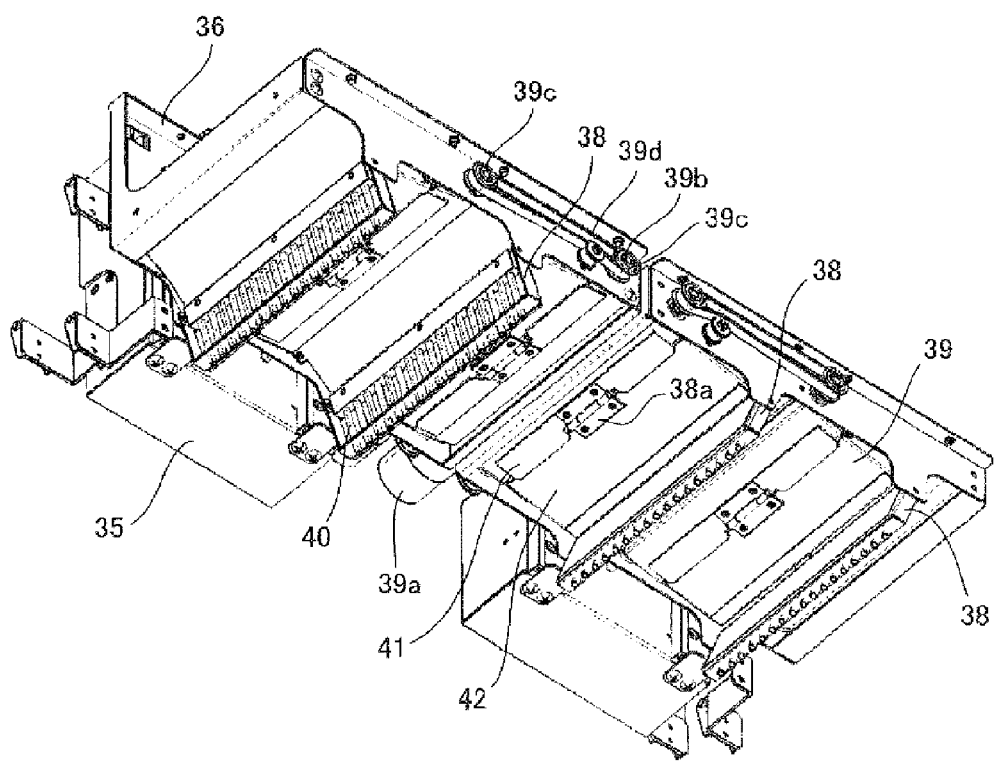
FIG. 6 is a lower perspective view of the medicine storing member shown in FIG. 1.

As shown in FIGS. 5 and 6, the medicine storing member 32 includes a supporter 35 anchored to the device body 3 and a body portion 36 supported by the supporter 35 to be lifted and lowered. The body portion 36 is lifted and lowered by a motor (not shown) in the supporter 35. Four medicine storing sections 37 are provided in the body portion 36. A bottom side of each of the medicine storing sections 37 comprises a first inclined plate 38 and a second inclined plate 39. The first inclined plate 38 is fixed to the body portion 36 and is bent at its midway portion. A plurality of brushes are integrated with a lower half portion of the first inclined plate 38 as protruding from a leading end. The second inclined plate 39 is provided to be pivoted about a spindle 39b by operation of a motor 39a. A pulley 39c is fixed to each of the spindles 39b. The second inclined plates 39 are thus synchronously pivoted through a belt 39d wound around the pulleys 39c. The second inclined plate 39 has a configuration similar to the bottom plate 27 of the aforementioned medicine receiving container 19. The second inclined plate comprises a first inclined section 41 and a second inclined section 42 that are pivotally connected to each other via a hinge 38a. Further, elastic sheets 43 are placed on the first inclined plate 38 and the second inclined plate 39 respectively. Further, as the second inclined plate 39 is positioned centrally, the ampoules can be accurately discharged to each of the medicine collecting sections 4 of the medicine collecting container 34. Moreover, if the first inclined plate 38 is tilted inwardly according to the position of the medicine collecting section 44, the receipt quantity of the ampoules 12 can increase. This can expand the medicine storing member 32 relative to the medicine collecting container 34, thus increasing the storage quantity of the ampoules 12.

The conveying member 33 includes a conveying belt 33a driven by a motor (not shown). The conveying member conveys the medicine collecting container 34 into the device body 3 and stops the medicine collecting container temporarily and thereafter conveys the medicine collecting container outwardly.

Partition plates 34a quadrisect the interior of the medicine collecting container 34 to define the medicine collecting sections 44. This is for coping with the maximum number of times in one day's prescription for one patient (e.g., morning, daytime, evening, night). Each of the medicine collecting sections 44 is sized to correspond to each of the medicine storing sections 37 of the medicine storing member 32.

1-4. Control Unit 7

Figure 7:
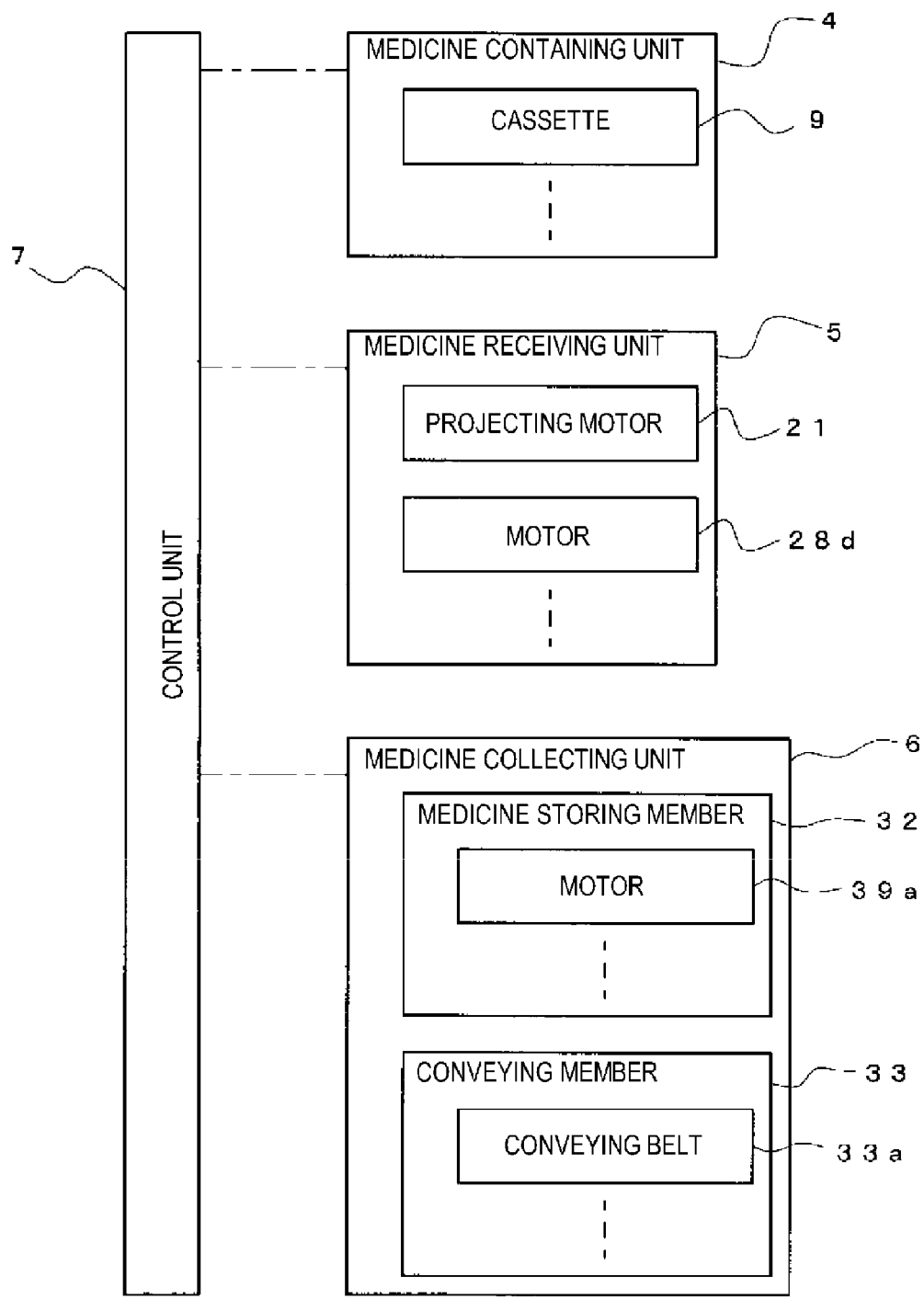
FIG. 7 is a block diagram of the medicine dispensing device in accordance with one embodiment.

As shown in FIG. 7, the control unit 7 controls various motors to allow the medicine receiving container 19 to move based on a prescription data inputted from a host computer. Further, the control unit allows associated medicines to be dispensed from the cassettes 9 of the medicine containing unit 4 and then allows the medicines to be collected in the medicine collecting container 34 through the medicine storing member 32. Thereafter, the control unit allows the medicine collecting container 34 to move in order to convey the collected medicines outward.

2. Operation

Figure 8:
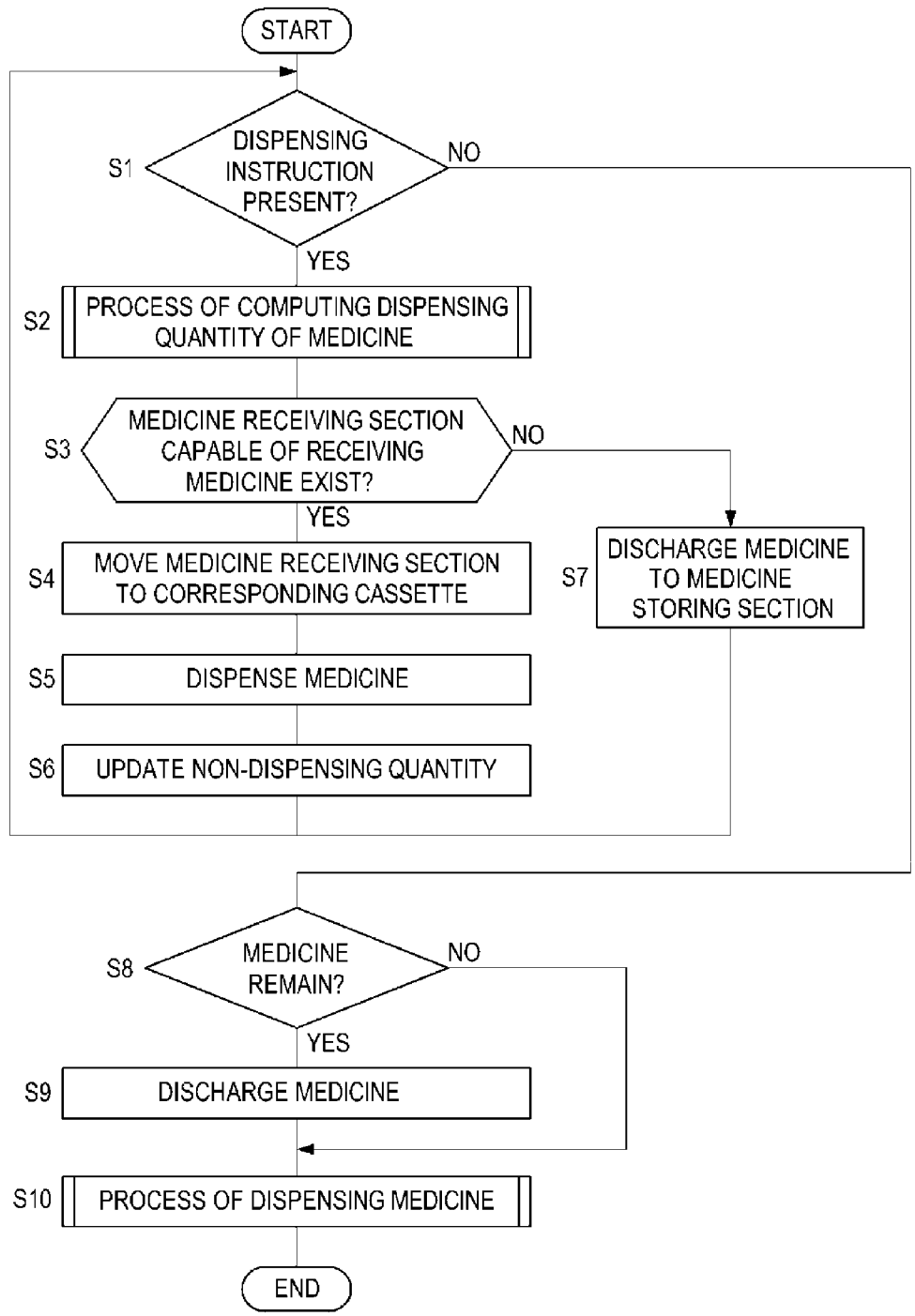
FIG. 8 is a flow chart showing operations of the medicine dispensing device in accordance with one embodiment.

Next, descriptions will be provided as to the operations of the medicine dispensing device constructed as described above with reference to a flow chart shown in FIG. 8.

First, it is determined, based on a prescription data, whether an instruction for dispensing medicines is present (Step S1). Where the dispensing instruction is present, a process of computing a dispensing quantity of medicines is performed (Step S2).

Figure 9:
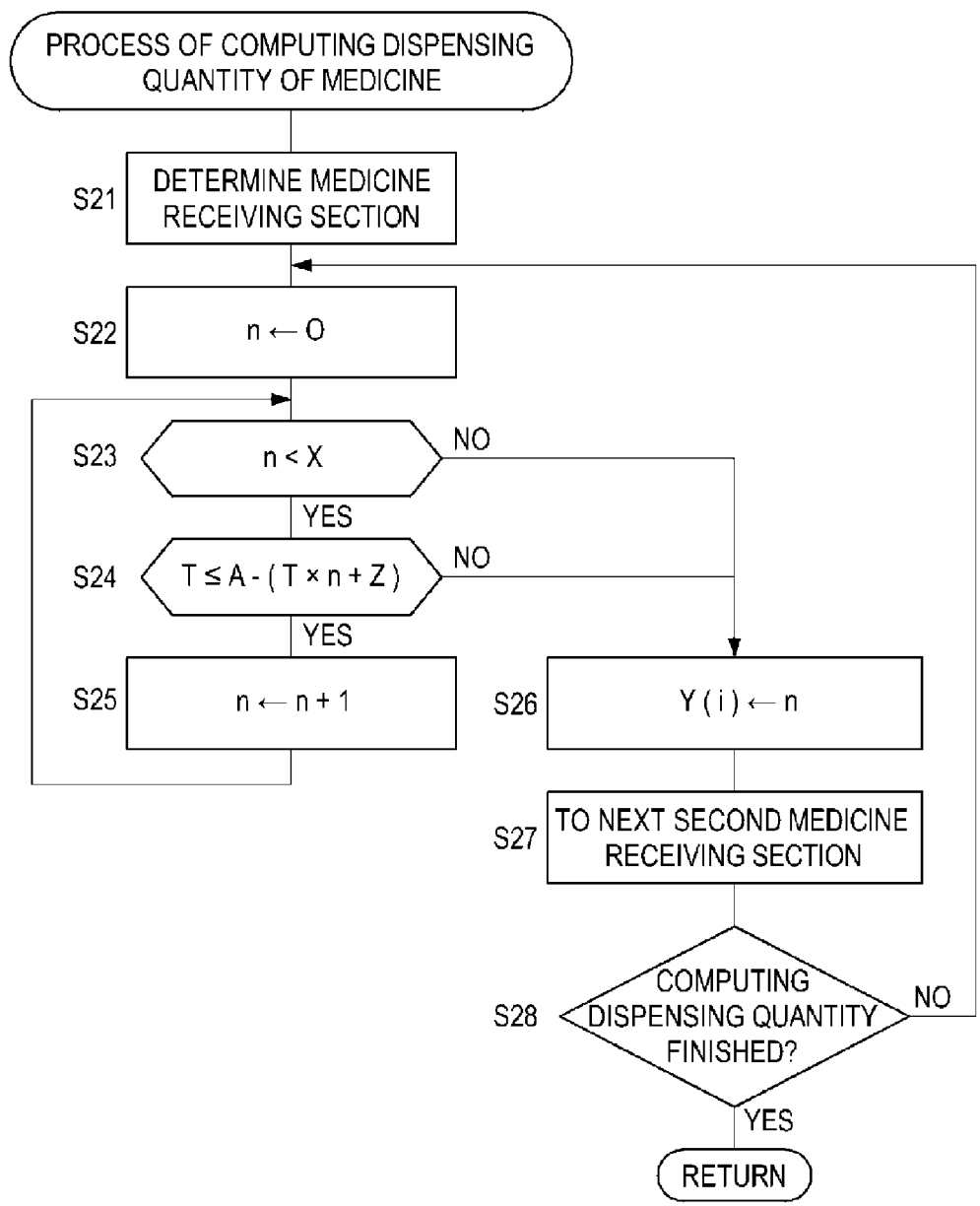
FIG. 9 is a flow chart showing a process of computing a dispensing quantity in FIG. 8.

In the process of computing the dispensing quantity of medicines, as shown in FIG. 9, it is determined which of the medicine receiving sections 26 in the medicine receiving container 19 the medicines are to be dispensed to (Step S21). In this embodiment, two medicine receiving sections 26 are provided. Thus, the first medicine receiving section is determined first, and thereafter the second medicine receiving section is determined in Step S27 as described below.

When the first medicine receiving section is determined, a dispensing quantity is initialized (n=0) (Step S22) and it is determined whether the dispensing quantity Y(i) is less than a non-dispensing quantity X (Step S23). Further, the dispensing quantity of the medicines is added (n+1) (Step S25) until the dispensing quantity Y(i) reaches to the non-dispensing quantity X or the following equation is satisfied (Step S24).

$$T \leq A - (T \times n + Z) \quad \text{[Equation 1]}$$

A: total capacity of medicine receiving section 26 (limit receipt quantity)
T: size of medicine
n: assumed quantity of dispensed medicines (number)
Z: initial capacity of medicine receiving section 26

The dispensing quantity Y(i) is added as explained above. As a result, when the value added as such exceeds the non-dispensing quantity X, or when the equation 1 is not satisfied in spite of the dispensing quantity Y(i) less than the non-dispensing quantity X and thus it is determined that the first medicine receiving section can receive medicines no more, the dispensing quantity Y(i) is determined as a current dispensing quantity (n) before adding (Step S26). Subsequently, the medicine receiving section 26, to which medicines are to be dispensed, is set to next second medicine receiving section (Step S27).

Thereafter, similar to the foregoing, the Step 21 to the Step S27 continue until the dispensing quantity of medicines for the second medicine receiving section is computed (Step 28).

After the dispensing quantity of medicines is computed, it is determined whether the medicine receiving section 26, to which medicine can be dispensed, exists (Step S3). If the medicine receiving section 26, to which medicine can be dispensed, exists, the medicine receiving section 26 is moved to the corresponding cassette 9 (Step S4). In this case, through the movement of the medicine receiving container 19, the first receiving section 26a is positioned to a position where corresponding medicines can be dispensed from the cassette 9 containing such medicines. Subsequently, the projecting pin 22 of the projecting unit 18 is projected to push in the rod 14 provided in the medicine containing unit 4, thus dispensing the medicines one at a time through the rotation of the rotor 13. By doing so, the medicines as many as the quantity previously computed in said Step S2 are dispensed to the medicine receiving section 26 (Step S5). If dispensing the medicines is finished, the non-dispensing quantity is updated based on the dispensing quantity (Step S6).

Thereafter, similar to the foregoing, the processes in the Step S4 to the Step S6 are continued until the medicine receiving section 26, to which medicine can be dispensed, exists no longer. In this case, dispensing medicines from the cassette 9 to each of the medicine receiving sections 26 is continued until the medicines as many as the computed dispensing quantity are dispensed to both the first medicine receiving section 26a and the second medicine receiving section 26b. As for dispensing the medicines from the cassette 9 to the second medicine receiving section, the medicine receiving container 19 is slidably moved to position the second medicine receiving section 26b to the projecting unit 18 since the projecting unit 18 is located at the first medicine receiving section 26a.

When dispensing various types of medicines to the first medicine receiving section 26a and the second medicine receiving section 26b, the order of dispensing such medicines can be set freely. For example, when dispensing one A medicine to the first medicine receiving section 26a and dispensing one A medicine and one B medicine to the second medicine receiving section 26b, the A medicine may be dispensed to the first medicine receiving section 26a and thereafter the one B medicine may be dispensed to the second medicine receiving section 26b first instead of the A medicine. Further, when dispensing one A medicine and one B medicine to the first medicine receiving section 26b and dispensing one A medicine to the second medicine receiving section 26b, the A medicine may be dispensed to the first medicine receiving section 26a and thereafter the B medicine is dispensed to the first medicine receiving section 26a prior to dispensing the A medicine to the second medicine receiving section 26b. Or, the one A medicine may be dispensed to the second medicine receiving section 26b first than the first medicine receiving section 26a. Receiving operation for medicines when using one medicine receiving section 26 will be described. For example, when the limit receipt quantity of the medicine receiving section is ten and six A medicines of a size 3 and six B medicines of a size 2 is to be dispensed, dispensing three A medicines to the medicine receiving section 26 does not allow the medicine receiving section 26 to receive more than that. Accordingly, the A medicines once received are dispensed from the medicine receiving section 26a to the medicine storing member 32. Subsequently, the medicine receiving section 26 is moved again and a second dispensing operation for three A medicines is performed. Thereafter, five B medicines are dispensed to the medicine receiving section 26 by a third dispensing operation and then the rest one B medicine is dispensed to the medicine receiving section 26 by a fourth dispensing operation. According to the foregoing, the dispensing operations are performed four times. On the contrary, if dispensing one set of four medicines including two A medicines and two B medicines, then the dispensing operations can be finished three times.

If dispensing medicines to the first medicine receiving section 26a and the second medicine receiving section 26b is finished, then the medicine receiving container 19 is moved to the medicine storing member 32 and all the dispensed medicines are discharged to each of the corresponding medicine storing sections 37 (Step S7). In this case, the first medicine receiving section 26a is positioned to the first medicine storing section of the medicine storing member 32 and the second medicine receiving section 26b is positioned to the second medicine storing section. Subsequently, the bottom plate 27 is pivoted to open the bottom side and the medicines are discharged concurrently in two places from each of the medicine receiving sections 26 to each of the corresponding medicine storing section 37. At this time, the receipt capacity of each medicine receiving section 26 is reset to 0.

If the dispensing instruction is absent in the Step S1, then it is determined whether medicines remains in each medicine receiving section 26 of the medicine receiving container 19 (Step S8). Such determination may be made, for example, based on whether medicines are dispensed from the cassette 9 to the medicine receiving section 26 and thereafter the medicines are dispensed from such a medicine receiving section 26 to the medicine storing member 32. If medicines remain in the medicine receiving section 26, the medicine receiving container 19 is moved to the rest two places among each of the medicine storing sections 27 of the medicine storing member 32 and the medicines are dispensed (Step S9). At this time, similar to the foregoing, the receipt capacity of each medicine receiving section 26 is reset to 0. Thereafter, a process of dispensing medicines from the medicine storing member 32 to the medicine collecting container 34 is performed (Step S10).

Figure 10:
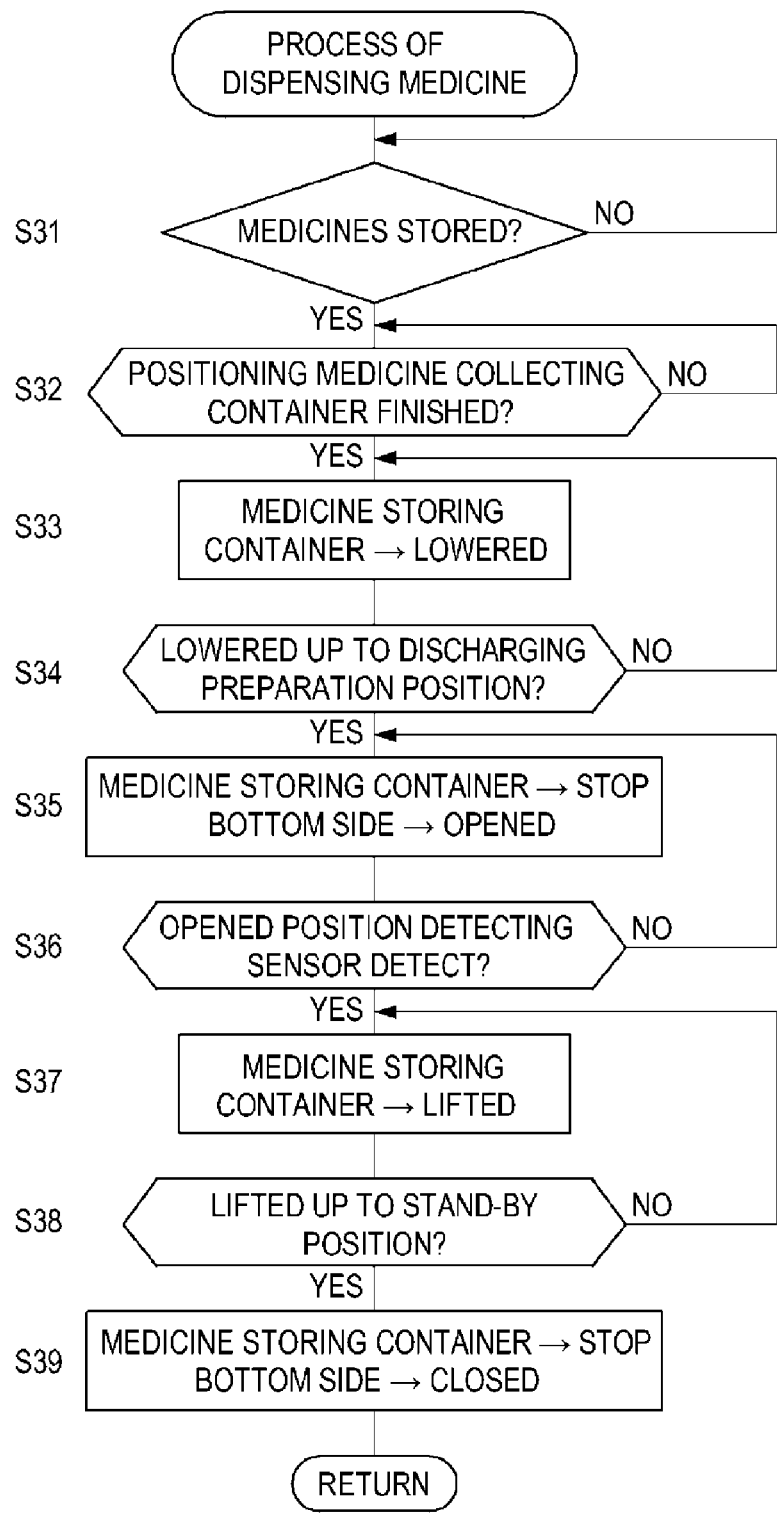
FIG. 10 is a flow chart showing a process of dispensing medicines in FIG. 8.

In said dispensing process, as shown by the flow chart in FIG. 10, it is first determined whether medicines are stored in all the medicine storing sections 37 of the medicine storing member 32 (Step S31). If storing the medicines is finished, the dispensing process stands by until the medicine collecting container 34 is positioned to a discharging position below the medicine storing sections (Step S32). If the medicine collecting container 34 is positioned to the discharging position, the medicine storing member 32 is lowered down (Step S33). Subsequently, if a lowering position detecting sensor (not shown) detects that the medicine storing member 32 is lowered down up to a discharging preparation position adjacent to the discharging position (Step S34), then the medicine storing member 32 is stopped and the second inclined plate 39 is pivoted to open the bottom side (Step S35). Pivoting of the second inclined plate 39 is continued until an opened position detecting sensor (not shown) detects such pivoting (Step S36). Thus, the stored medicines are dispensed together to each medicine collecting section 44 of the medicine collecting container 34. Thereafter, if the second inclined plate 39 is pivoted to a predetermined position, then the tablet storing member 32 is lifted to a discharging stand-by position (Step S37). If a stand-by position detecting sensor (not shown) detects the medicine storing member 32 (Step S38), then lifting of the medicine storing member 32 is stopped and the second inclined plate 39 is pivoted to close the bottom side (Step S39). Thereafter, the medicine collecting container 34 with the medicines dispensed therein is conveyed out for next processes and a next medicine collecting container 34 is conveyed in.

As described above, according to the configuration of the foregoing embodiment, the pair of the medicine receiving sections 26 are moved upwardly and downwardly leftward and rightward as they are adjacent to each other, thus allowing for simplified construction and a low-cost manufacture. Moreover, the medicine receiving container 19 is horizontally moved with respect to the projecting unit 18 and thus each medicine receiving section 26 is combined with the projecting unit 18, thereby allowing for high-speed reliable dispensing operation for the medicines. In particular, this is effective in continuously dispensing medicines from the same cassette 9. Further, medicines are temporarily or previously stored in the medicine storing member 32 disposed in the vicinity of the medicine collecting container 34 and stored medicines are concurrently discharged to the medicine collecting container 34, thereby allowing for rapid dispensing operation and eliminating troubles such as breakage in the ampoule 12 (medicine).

3. Another Embodiment

The present invention should not be limited to the foregoing embodiment. Various variations and modifications may be made within the subject matter of the following claims.

According to the foregoing embodiment, medicines are stored in the medicine storing member 32 previously to being dispensed from the medicine receiving container 19 to the medicine collecting container 34. However, the medicine storing member 32 is not necessarily required. Medicines may be dispensed directly from the medicine receiving container 19 to each of the medicine collecting section 44 of the medicine collecting container 34.

The medicine receiving container 19 is configured such that the pair of the medicine receiving sections 26 are moved upwardly and downwardly leftward and rightward as they are adjacent to each other. However, each medicine receiving section 26 may be independently moved upwardly and downwardly leftward and rightward. This allows for a more high-speed medicine dispensing process, since one of the medicine receiving sections 26 can receive medicines from one cassette 9 while the other of the medicine receiving sections 26 are receiving medicines from another cassette 9 (regardless of whether the medicines are the same or not).

3-2. Third Embodiment

Figure 11:
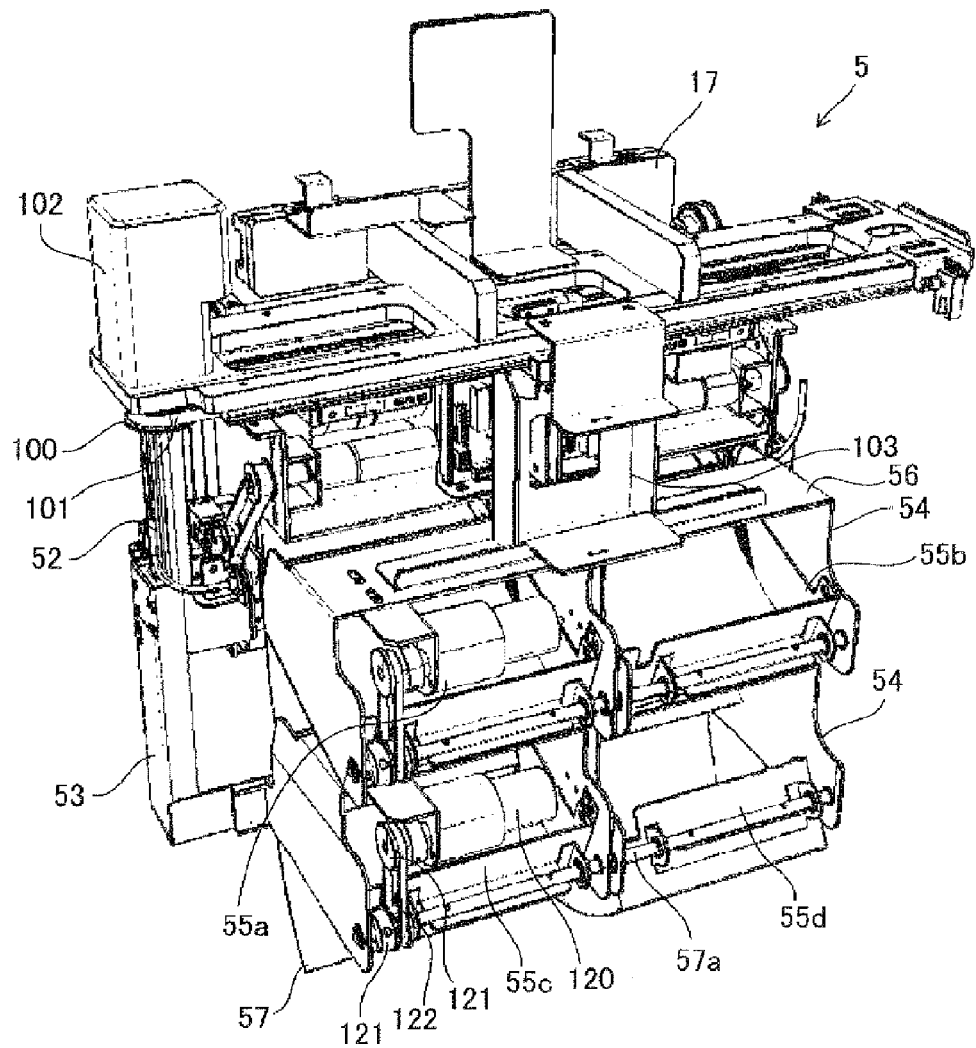
FIG. 11 is a frontal perspective view of a medicine receiving unit in accordance with another embodiment.
Figure 12:
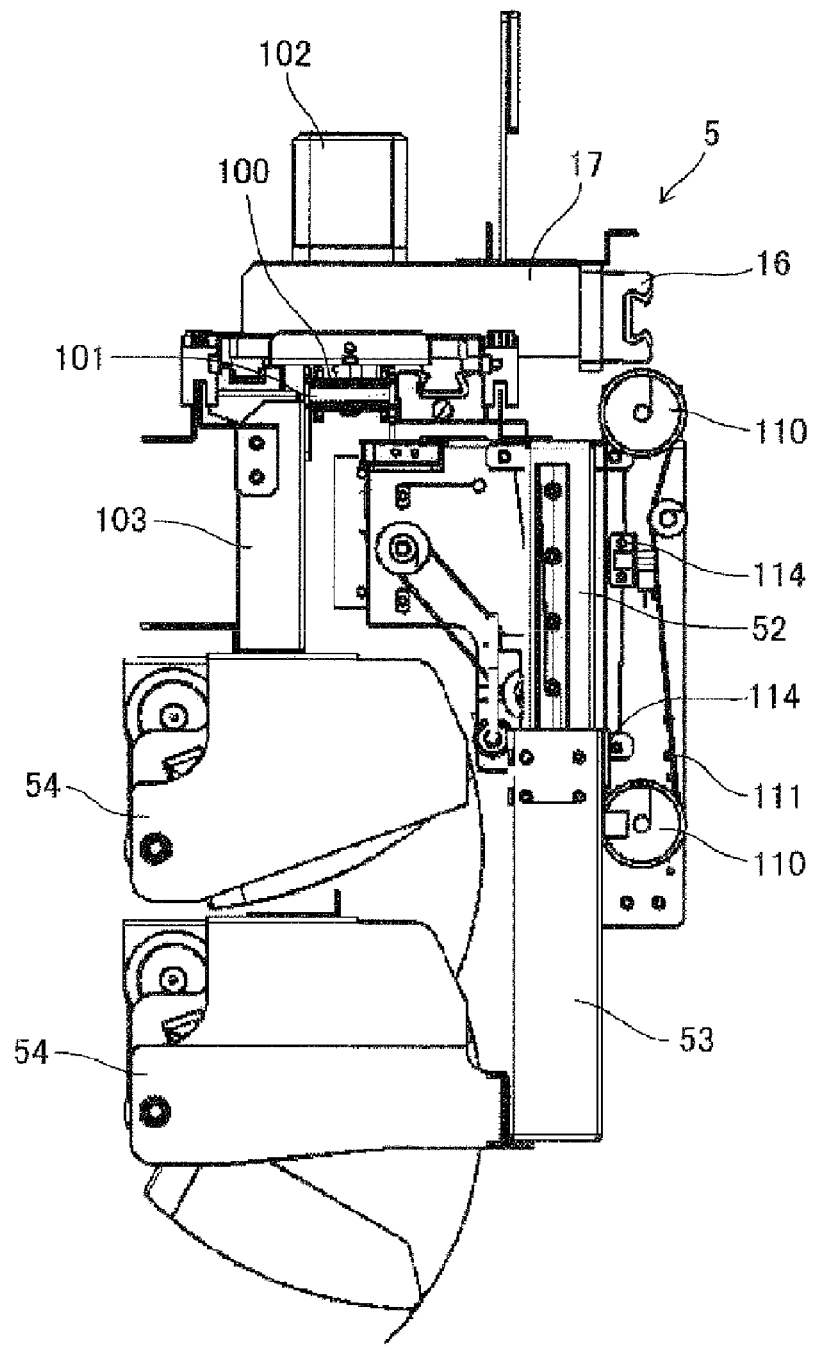
FIG. 12 is a side view of the medicine receiving unit in accordance with another embodiment.
Figure 13:
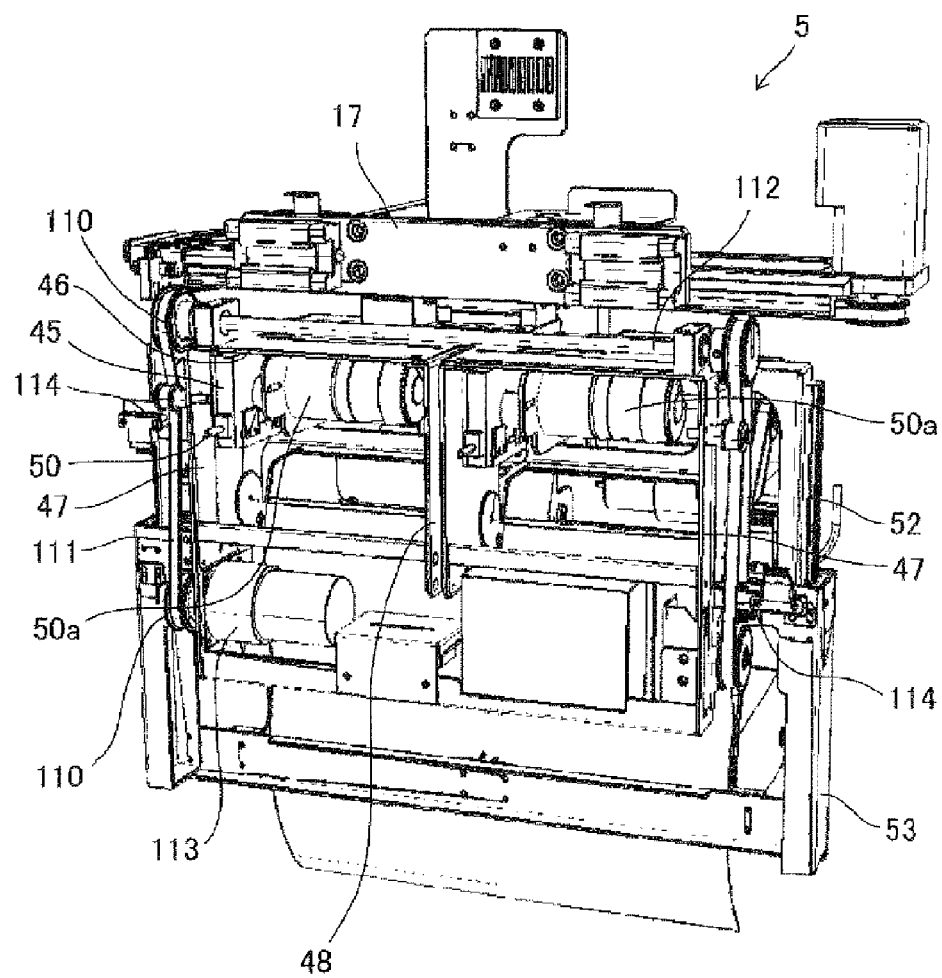
FIG. 13 is a rear perspective view of the medicine receiving unit in accordance with another embodiment.

According to the foregoing embodiment, the medicine receiving unit 5 includes the medicine receiving container 19 comprised of two medicine receiving sections 26. However, for example, as shown in FIGS. 11 to 13, the medicine receiving unit may include two medicine receiving containers 19, each of which is comprised of two medicine receiving sections 26.

Specifically, similar to the foregoing, the medicine receiving unit 5 includes: a pair of the vertical rails 15 located left and right on the front of the device body 3; the horizontal rail 16 provided to the vertical rails 15 to be upwardly and downwardly reciprocable; and the slide base 17 provided to the horizontal rail 16 to be leftward and rightward reciprocable. Further, a horizontal drive mechanism for driving each medicine receiving container 19 leftward and rightward is provided in the slide base 17.

The horizontal drive mechanism includes a pair of pulleys 100 (one of them is not shown) and a belt 100 wound between the pulleys. One of the pulleys is normally and reversely rotated by operation of a motor 102. Further, each medicine receiving container 19 is connected to the belt via a connection piece 103. The connection position is a midway point of each straight section of the belt 101 when each medicine receiving container 19 is vertically juxtaposed in the middle. If the motor is operated normally and reversely from such a state, each medicine receiving container 19 is reciprocated leftward and rightward.

Further, a projecting unit 45 is attached to the lower surface of the slide base 17. The projecting unit 45 includes: a top plate 46; both side plates 47 extending downwardly from both ends of the top plate; and a partition plate 48 extending downwardly from a midway portion of a lower surface of the top plate to partition both sides. A motor 50a is provided in the top plate 46 in each of two sections divided by the partition plate 38. The motors 50a are capable of advancing and retracting the respective projecting pins 50 through a rack and a pinion (not shown).

A vertical drive mechanism is provided at both sides of the projecting unit 50. The vertical drive mechanism includes a pair of first sliders 52 extending downwardly from the both side plates 47 of the projecting unit 50 and a second slider 53 of a general U shape that is upwardly and downwardly slidably provided on the first sliders 52. Pulleys 110 are provided in upper portions of the both ends of the top plate 46 and the both side plates 47 of the projecting unit 50 respectively. Belts 110 are wound between the pulleys 110 located up and down in the one end and between the pulleys 110 located up and down in the opposite end. The pulleys 110 located up are connected by a spindle 112. The pulley 110 located down in the one end is rotated by operation of a motor 113. Each medicine receiving container 54 is connected to each belt 111 via a connection piece 114 respectively. The connection position is each straight section of the belts 111 located forward and backward. Accordingly, as the motor 113 is operated normally and reversely, the second slider 53 is lifted and lowered through the pulleys 110 and the belts 111 and each medicine receiving container 19 is moved in opposite vertical directions.

Each medicine receiving section 55 constituting the medicine receiving container 19 is comprised of a generally U-shaped frame 56 and a bottom plate 57 covering both a bottom side and one lateral side of the frame 56. Each bottom plate 57 is provided to pivot about a common spindle 57a. As a motor 120 (e.g., stepping motor) is operated normally and reversely, a power therefrom is transmitted to the bottom plate via pulleys 121 and a belt 122. Thus, the bottom of each medicine receiving section 26 synchronously opens and closes the bottom side and the lateral side.

The medicine receiving unit 5 includes the two medicine receiving containers each including the two medicine receiving sections, thus moving each medicine receiving container upwardly and downwardly leftward and rightward as shown in FIGS. 14(a) to 14(i).

Figure 14:
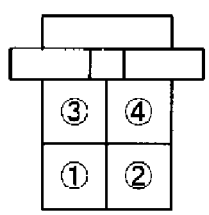
FIG. 14 illustrates example operations of medicine receiving sections shown in FIG. 11.
Figure 14:
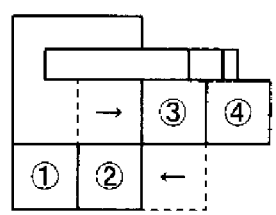
Figure 14:
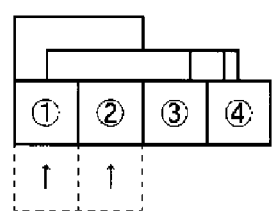
Figure 14:
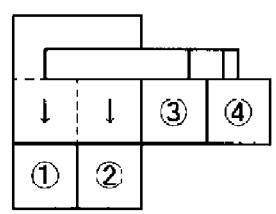
Figure 14:
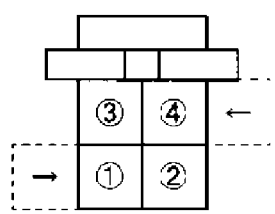
Figure 14:
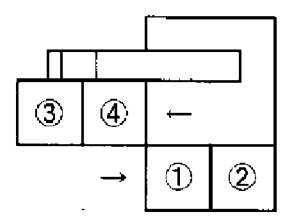
Figure 14:
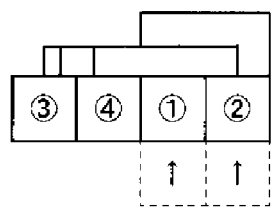
Figure 14:
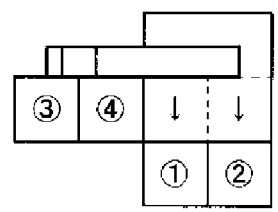
Figure 14:
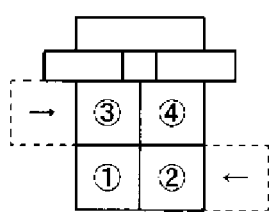

Specifically, as shown in FIG. 14(a), one set including third and fourth medicine receiving section 26c and 26d and the other set including the first and second medicine receiving section 26a and 26b are moved leftward and rightward respectively from a state wherein they are vertically juxtaposed. Subsequently, if they are positioned such that they are not vertically juxtaposed as shown in FIG. 14(b), then, as shown in FIG. 14(c), the first and second medicine receiving sections 26a and 26b are moved upwardly and each medicine receiving section 26a to 26d is aligned in line in that order. Further, when changing leftward and rightward positions between the medicine receiving sections 26a and 26b and the medicine receiving sections 26c and 26d, operations shown in FIGS. 14(d) and 14(e) may be performed for return to the initial position. Thereafter, as shown in FIGS. 14(f) and 14(g), the operations opposite to the foregoing may be performed. Further, the return to the initial position may be done through operations shown in FIGS. 14(h) and 14(i). As described above, since each of the medicine receiving containers 19 comprising two medicine receiving sections 26a, 26b or two medicine receiving section 26c, 26d is moved upwardly and downwardly and leftward and rightward, any of the medicine receiving sections 26a to 26d can receive the medicines dispensed from the cassettes 9.

The movement of the above-described medicine receiving unit 5 may be made as follows.

Figure 15:
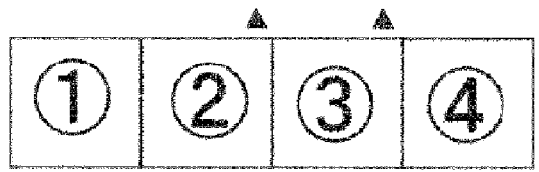
FIG. 15 illustrates further example operations of the medicine receiving sections shown in FIG. 11.
Figure 15:
Figure 15:
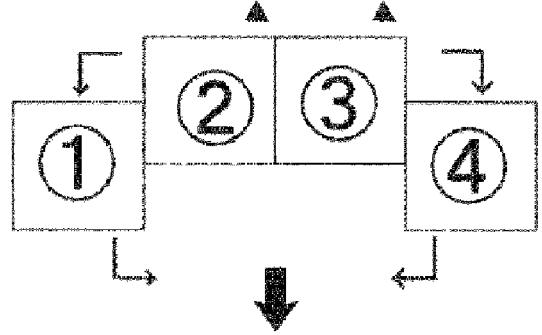
Figure 15:
Figure 15:
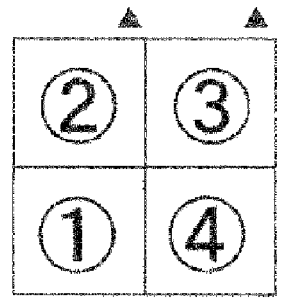
Figure 15:
Figure 15:
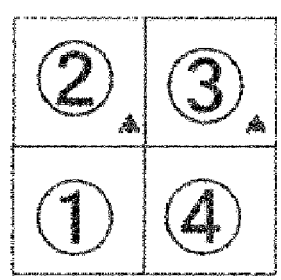

Specifically, as shown in FIG. 15, four medicine receiving sections are referred to as first to fourth medicine receiving sections 55a to 55d (in FIG. 15, the medicine receiving sections are denoted by numerical characters 1 to 4 encircled by a circle) in the order from one end. The first medicine receiving section 55a and the fourth medicine receiving section 55d can be moved upwardly and downwardly and leftward and rightward relative to the second medicine receiving section 55b and the third medicine receiving section 55c that are located centrally. In FIG. 15, triangles indicate the positions of the projecting pins 50. When dispensing medicines from the cassettes 9 to the second medicine receiving section 55b and the third medicine receiving section 55c, each of the medicine receiving sections 55a to 55d is positioned as shown in FIG. 15(a). Subsequently, as shown in FIG. 15(b), the first medicine receiving section 55a and the fourth medicine receiving section 55d are moved downwardly and then moved toward each other from the state shown in FIG. 15(a) and into the state shown in FIG. 15(c), such that they are positioned under the second medicine receiving section 55b and the third medicine receiving section 55c. Thereafter, all the medicine receiving sections 55a to 55d are moved upward. Then, the first medicine receiving section 55a and the fourth medicine receiving section 55d can receive the medicines that are dispensed from the cassettes 9 by means of the projecting pins 50 as shown in FIG. 15(d).

Figure 16:
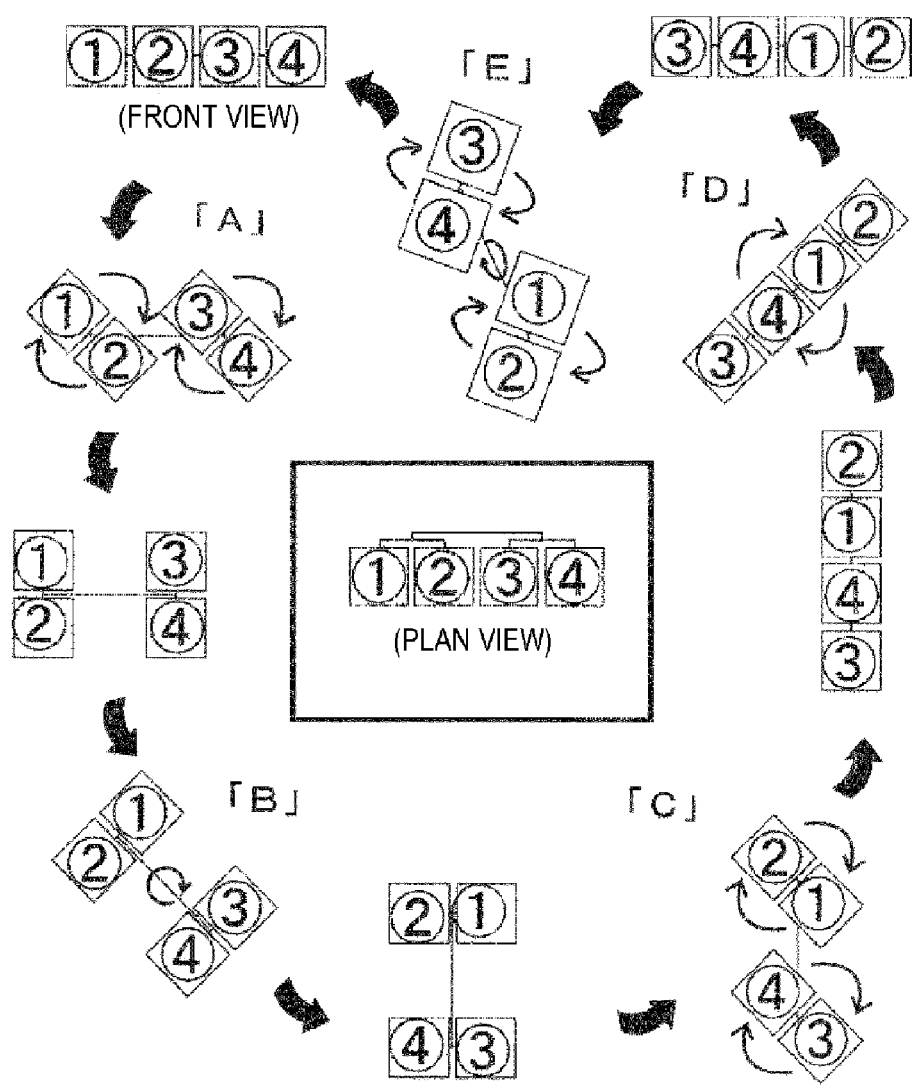
FIG. 16 illustrates still further example operations of the medicine receiving sections shown in FIG. 11.

Further, as shown in FIG. 16, the medicine receiving unit 5 may be configured to move four medicine receiving sections 55a to 55d (in FIG. 16, the medicine receiving sections are denoted by numerical characters 1 to 4 encircled by a circle). For example, as shown in FIG. 16, the first medicine receiving section 55a and the second medicine receiving section 55b are pivotably interconnected by a link. Further, the third medicine receiving section 55c and the fourth medicine receiving section 55d are pivotably interconnected by a link. Furthermore, both of the links are pivotally interconnected by a link. Thus, each of the medicine receiving sections 55a to 55d can be arranged with various arrangement patterns shown in FIG. 16. The arrangement patterns for each medicine receiving section 55a to 55d can be changed such that medicines can be dispensed to any one of the medicine receiving sections 55a to 55d from the cassettes 9 that are mounted at both sides and arranged vertically (in particular, the cassettes 9 located at four corners).

Further, the number of the medicine receiving sections 26 is not limited to two or four. It may be three or five or more.

Further, preferably, an orientation changing container 61 for changing the orientation of the medicines may be separately provided between the medicine receiving unit 5 and the medicine storing member 32 in order to smoothly execute delivery of the medicines to the medicine storing member 32.

Figure 17:
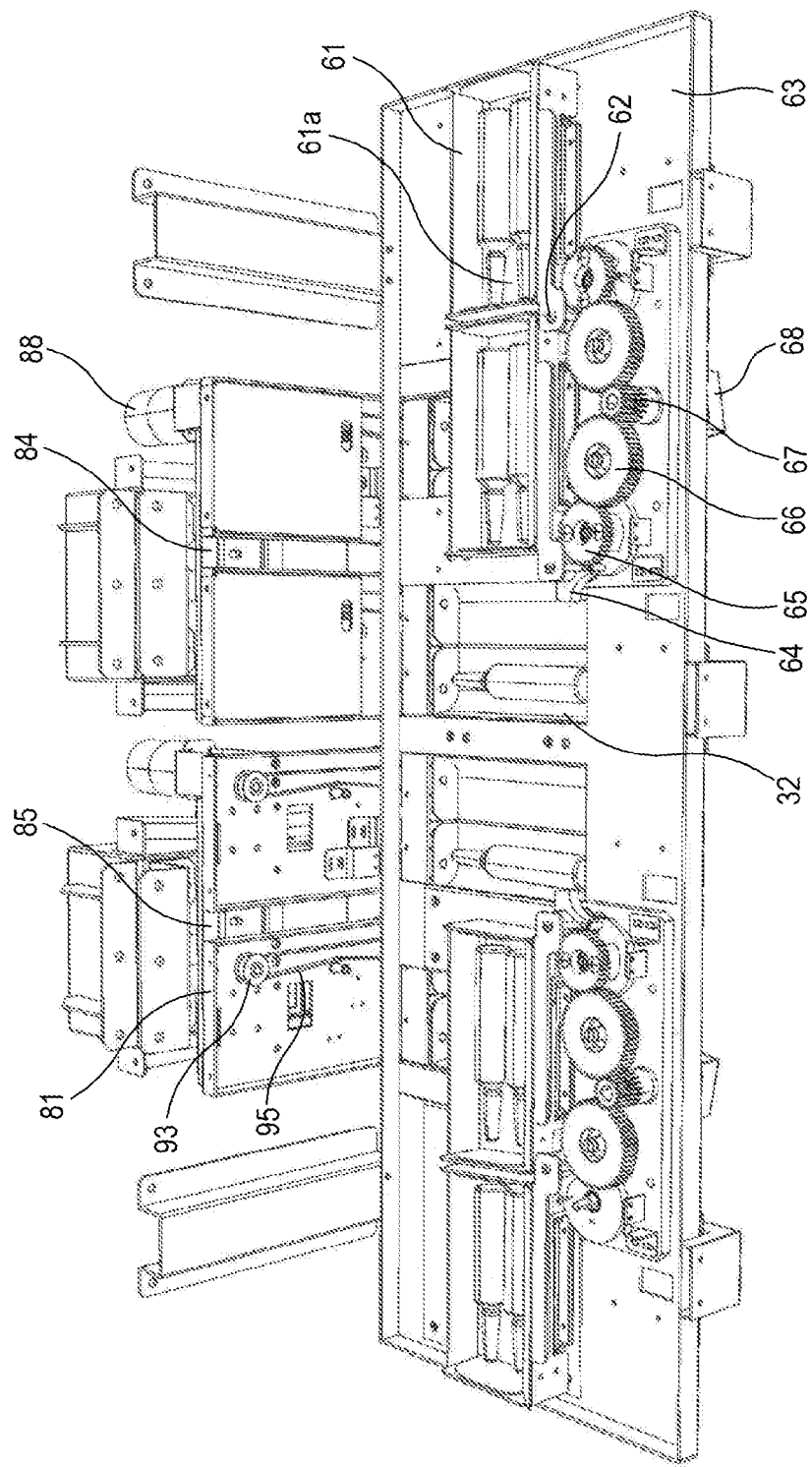
FIG. 17 is a perspective view showing a medicine storing member and other members adjacent thereto in accordance with another embodiment.
Figure 18:
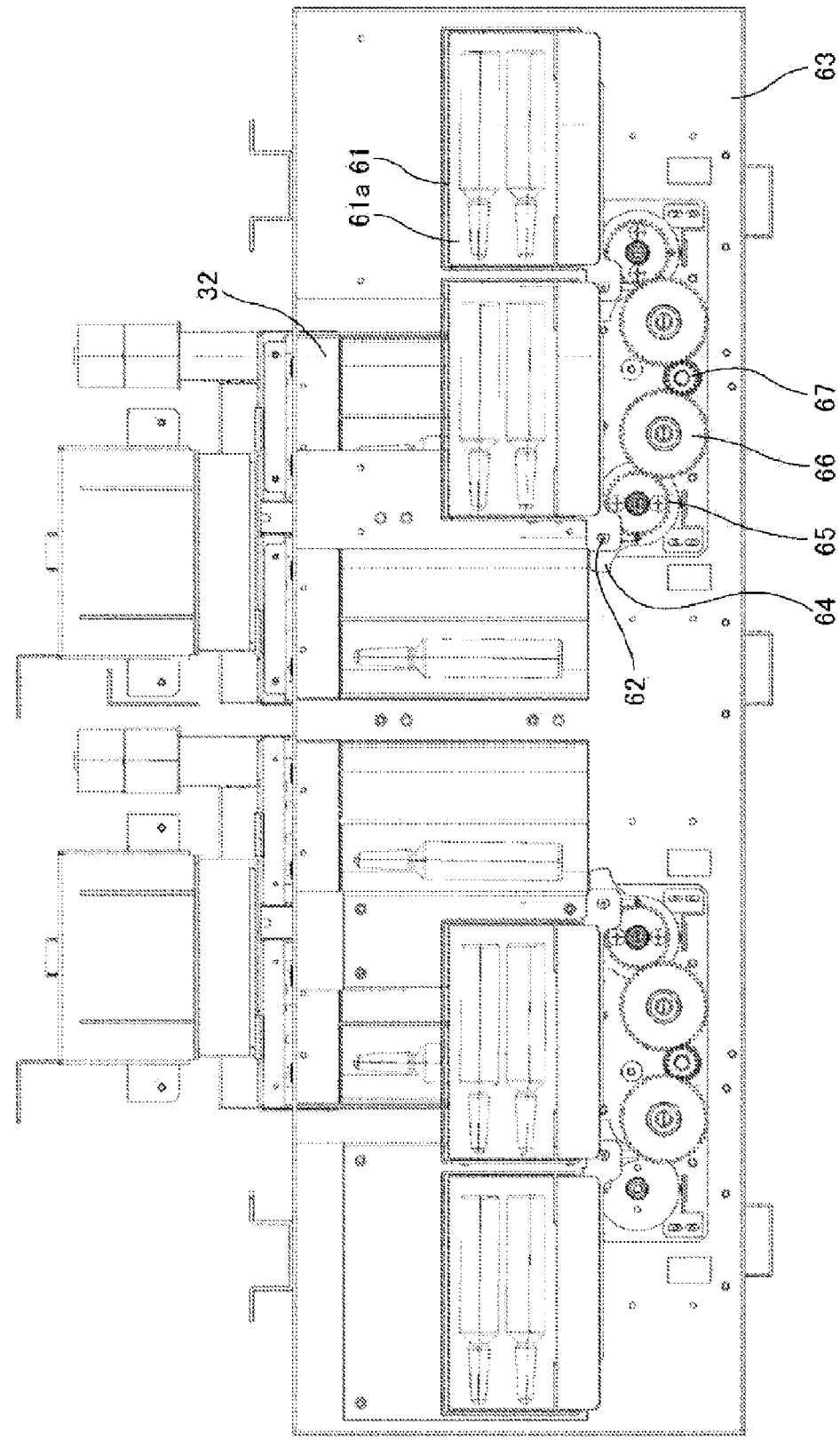
FIG. 18 is a plan view of FIG. 17.
Figure 19:
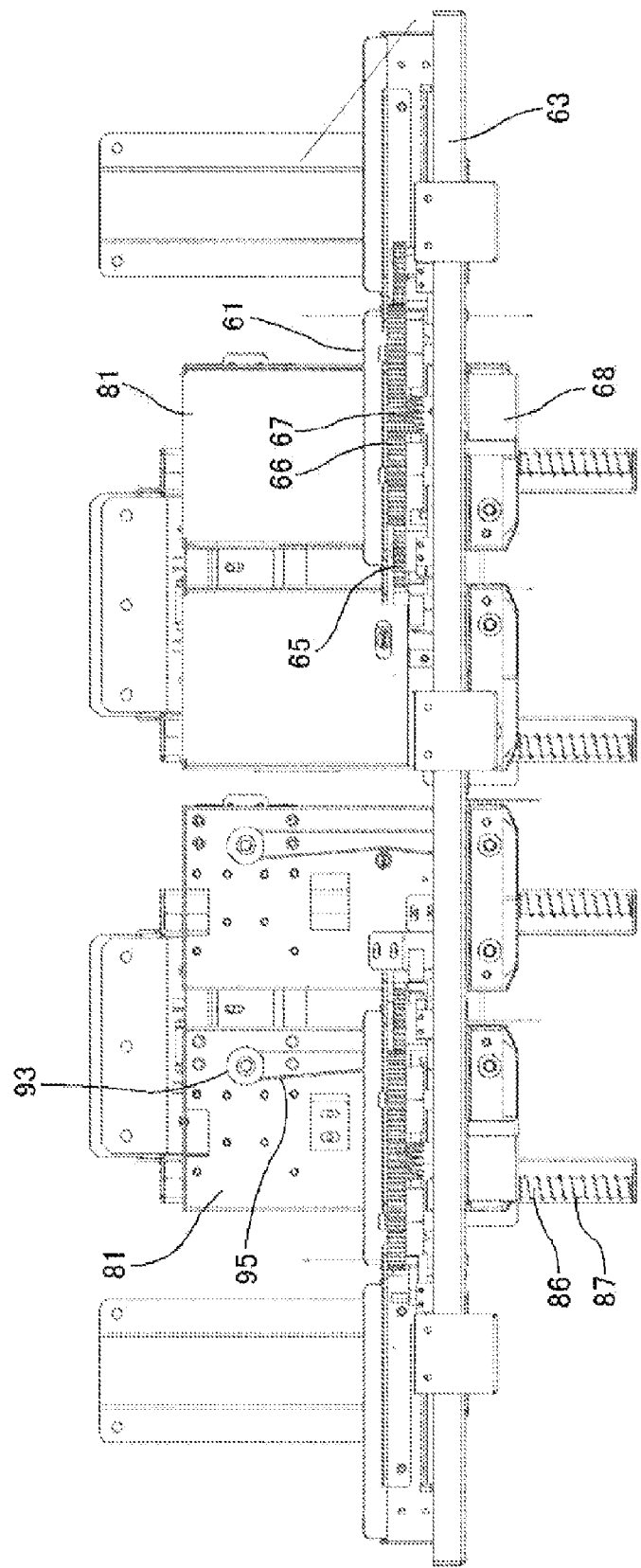
FIG. 19 is a front view of FIG. 17.

Specifically, as shown in FIGS. 17 to 19, the orientation changing container 61 is pivoted in a horizontal plane about a spindle 62 provided in one end of one side edge in a range of approximately 90 degrees between a transverse orientation position in the conveyance direction of the medicine collecting container 34 (in FIG. 17, in a right direction) and a longitudinal orientation position orthogonal to the transverse orientation position.

A bottom plate 61a of the orientation changing container 61 is pivotally provided about a rotating shaft (not shown) in the one side edge. The bottom plate 61a is supported on an upper surface of a support plate 63 to maintain a closed state. When the bottom plate reaches the medicine storing member 32, the bottom plate become free from support caused by the upper surface and is thus opened due to its own weight. Further, when the bottom plate 61a reaches the upper surface of the support plate 63 from the medicine storing member 32, the bottom plate automatically returns to the closed state due to pressure exerted thereto.

The spindle 62 incorporates a first cam 64. A power from a motor 68 is transmitted to the first cam via a second cam 65, a driven gear 66 and a drive gear 67.

The first cam 64 includes a first arm portion 69 extending from the spindle 62 in opposite directions and a second arm portion 70 extending orthogonally to the first arm portion 69. A cutout groove 71 is formed in the middle of the second arm portion 70 from a leading end. Further, first circular arc surfaces 72 are formed toward the first arm portion 69 in both sides of the second arm portion 70 respectively.

The second cam 65 is rotatably provided about a spindle 73 in the vicinity of the first cam 64. The second cam 65 includes a larger-diameter portion 74 and a smaller-diameter portion 75 integrated with a central portion of the larger-diameter portion. The smaller-diameter portion 75 slidably abuts the first circular arc surface 72 of the first cam 62 at its outer periphery surface to restrict a rotation position of the first cam 64. Further, second circular arc surfaces 76 are formed symmetrically at two places in the smaller-diameter portion 75. A protrusion 77 is formed near an outer periphery of the larger-diameter portion 74 so as to bisect one of the second circular arc surfaces 76 of the smaller-diameter portion 75. The protrusion 77 engages and disengages from the cutout groove 71 of the first cam 64. When the protrusion engages the cutout groove, the protrusion allows the first cam 64 to interlock with the second cam 64 and to rotate thereby. Further, a gear (not shown) is formed along the outer periphery of the larger-diameter portion 74.

The driven gear 66 comprises a larger-diameter gear 78 and a smaller-diameter gear (not shown). The smaller-diameter gear is placed into mesh with the gear (not shown) formed in the larger-diameter portion 74 of the second cam 65.

The drive gear 67 is integrated with a rotating shaft of the motor 68 and is placed into mesh with the driven gear 66. The drive gear 67 is in mesh with each driven gear 66 of the two orientation changing containers 61 placed closely to each other. Thus, both of the orientation changing containers 61 can be synchronously pivoted through the drive gear 67.

Figure 21:
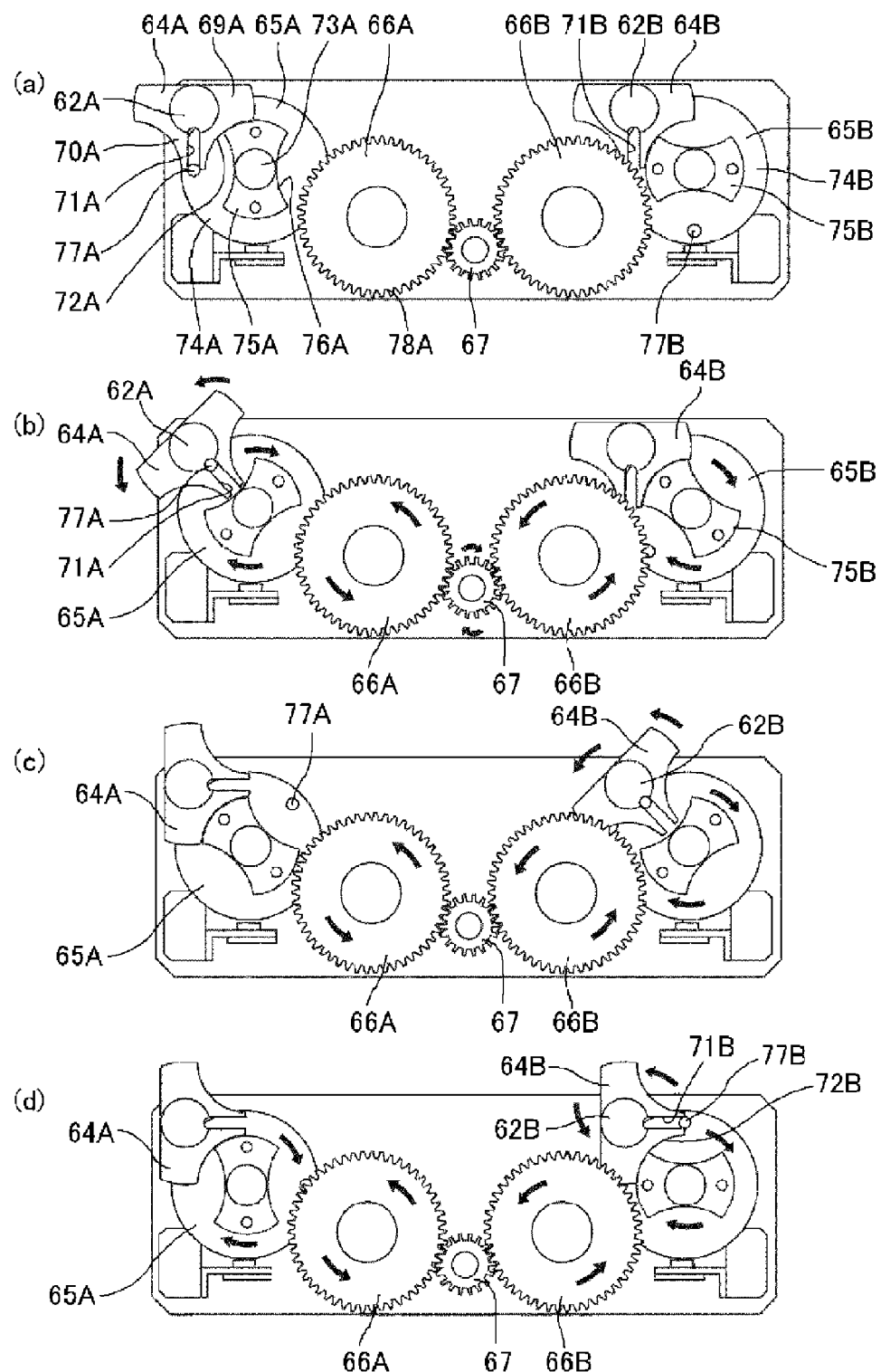
FIG. 21 illustrates a mechanism for performing rotating of the orientation changing containers shown in FIG. 20.

The orientation changing containers 61 in adjacent two places are configured to begin pivoting at a different time and to then be pivoted (hereinafter, referring to two orientation changing containers located right in FIG. 17, a suffix A is added to the left one and a suffix B is added to the right one.) Specifically, as shown in FIG. 21(a), the second cams 65A, 65B are placed as the smaller diameter portion 75A and the smaller diameter portion 75B are offset by 90 degrees in a rotation direction. Accordingly, if operation of the motor 68 rotates each of the driven gears 66A, 66B in a counterclockwise direction through the drive gear 67, each component operates as follows.

Figure 20:
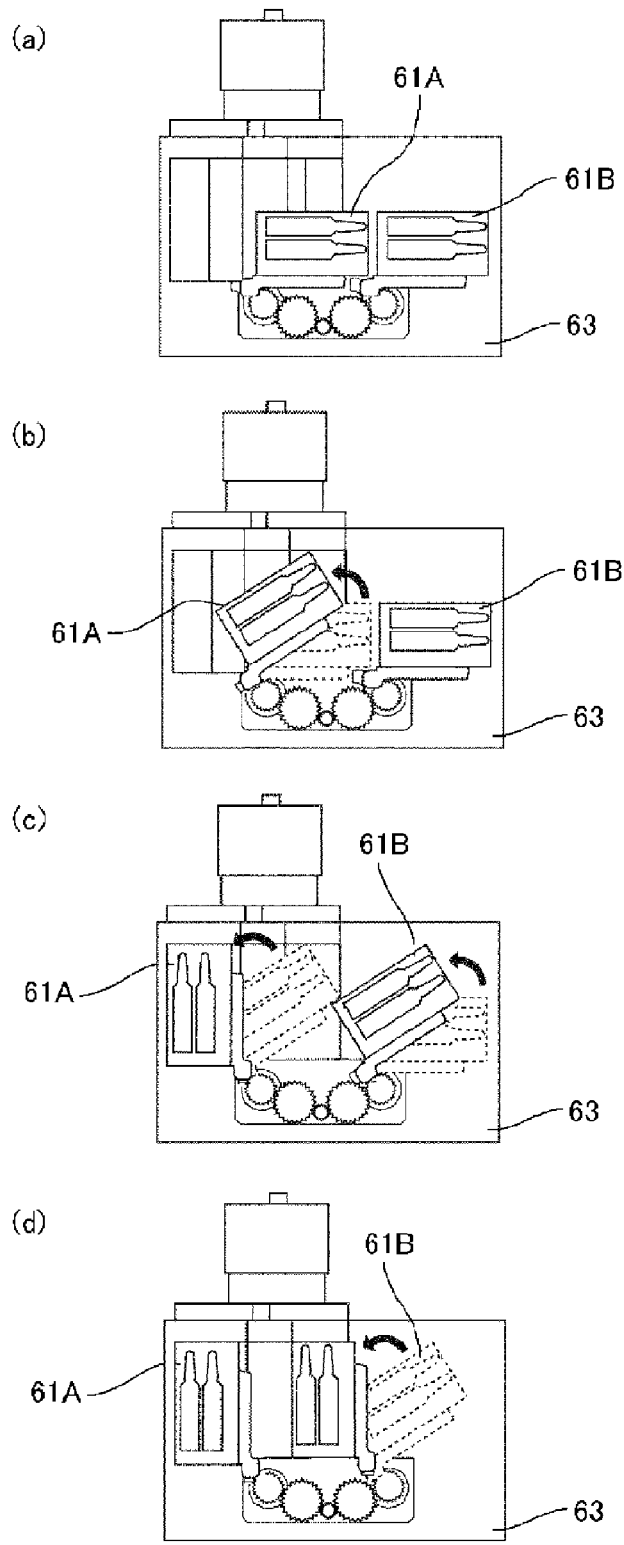
FIG. 20 diagrammatically illustrates operations of orientation changing containers located in two places in the right-hand side of FIG. 17.

In the left-hand side, the protrusion 77A of the second cam 65A enters into the cutout groove 71A of the first cam 64A to thus rotate the first cam 64A in the counterclockwise direction about the spindle 62A as shown in FIG. 21(b). As a result, as shown in FIG. 20(b), the orientation changing container 61A begins to pivot from the position shown in FIG. 20(a). Subsequently, when the first cam portion 64A is rotated by 90 degrees, the protrusion 77A disengages from the cutout groove 71A and the first cam portion 64A stops. Then, as shown in FIG. 20(c), the orientation changing container 61A is positioned to the longitudinal orientation position. At this time, the bottom plate 61a of the orientation changing container 61A loses the support caused by the support plate 63 and is opened, and thus, the medicines contained in the orientation changing container are discharged to the medicine storing member 32.

Further, in the right-hand side, while the orientation changing container 61A is being pivoted, the outer peripheral surface of the smaller-diameter portion 75B of the second cam 65B slides on the first circular arc surface 72B of the first cam 64B. This restrains the rotation of the first cam 64B, thus maintaining the orientation changing container 61B in the horizontal orientation position. Subsequently, when the orientation changing container 61A is pivoted up to the horizontal orientation position, the protrusion 77B of the second cam 65B enters into the cutout groove 71B of the first cam 64B and rotates the first cam 64B in the counterclockwise direction about the spindle 62B, as shown in FIG. 21(c). As a result, the orientation changing container 61B begins to pivot. Subsequently, as shown in FIG. 21(d), when the first cam portion 64B is rotated by 90 degrees, the protrusion 77B disengages from the cutout groove 71B and the first cam portion 64B stops. Thus, as shown in FIG. 20(d), the orientation changing container 61B is in the longitudinal orientation position and, similar to the foregoing, the medicines contained in the orientation changing container are discharged to the medicine storing member 32.

As described above, the orientation changing container 61A is first pivoted from the horizontal orientation position to the longitudinal orientation position and thereafter the orientation changing container 61B begins its pivoting and is pivoted from the horizontal orientation position to the longitudinal orientation position. Accordingly, the orientation changing containers 61A and 61B can be easily smoothly pivoted without any interference with each other within a limited area.

In case the orientation changing containers 61A and 61b are pivoted from the longitudinal orientation position to the horizontal orientation position, the motor 66 may be reversely operated so that operations opposite to the foregoing can be performed. The two left-hand orientation changing containers 61 are axisymmetric with the above-described two right-hand orientation changing containers and have the same basic operations as those of the two right-hand orientation changing containers. Thus, descriptions will be omitted on the two left-hand orientation changing containers.

According to the foregoing embodiment, one motor drives the two orientation changing containers 61. However, a motor provided separately may normally and reversely pivot each of the orientation changing containers 61 via gears.

Further, according to the foregoing embodiment, the medicine storing member 32 is configured to be lifted and lowered to open and close the second inclined plate 39 with respect to the first inclined plate 38. The medicine storing member may be configured as follows.

Figure 22:
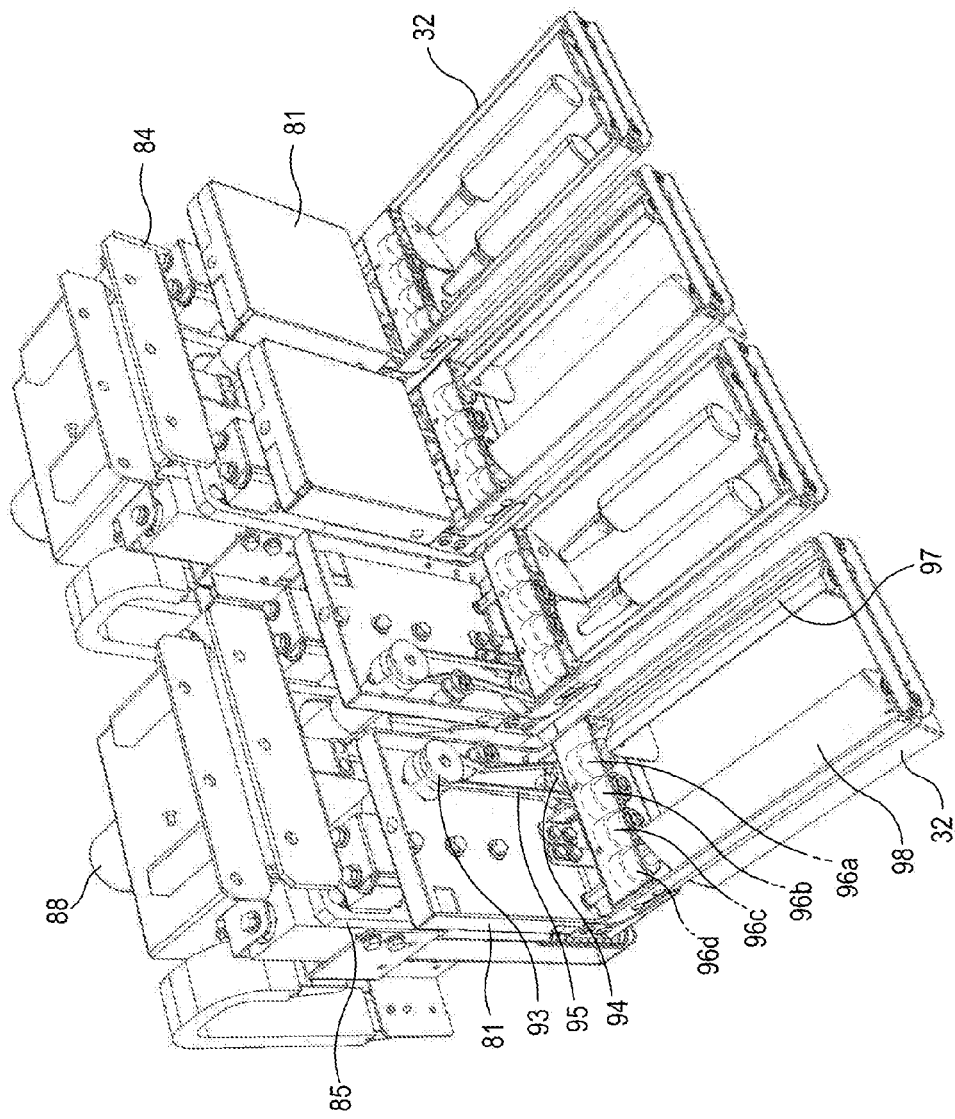
FIG. 22 is a perspective view showing a medicine storing member and other members adjacent thereto in accordance with yet another embodiment.
Figure 23:
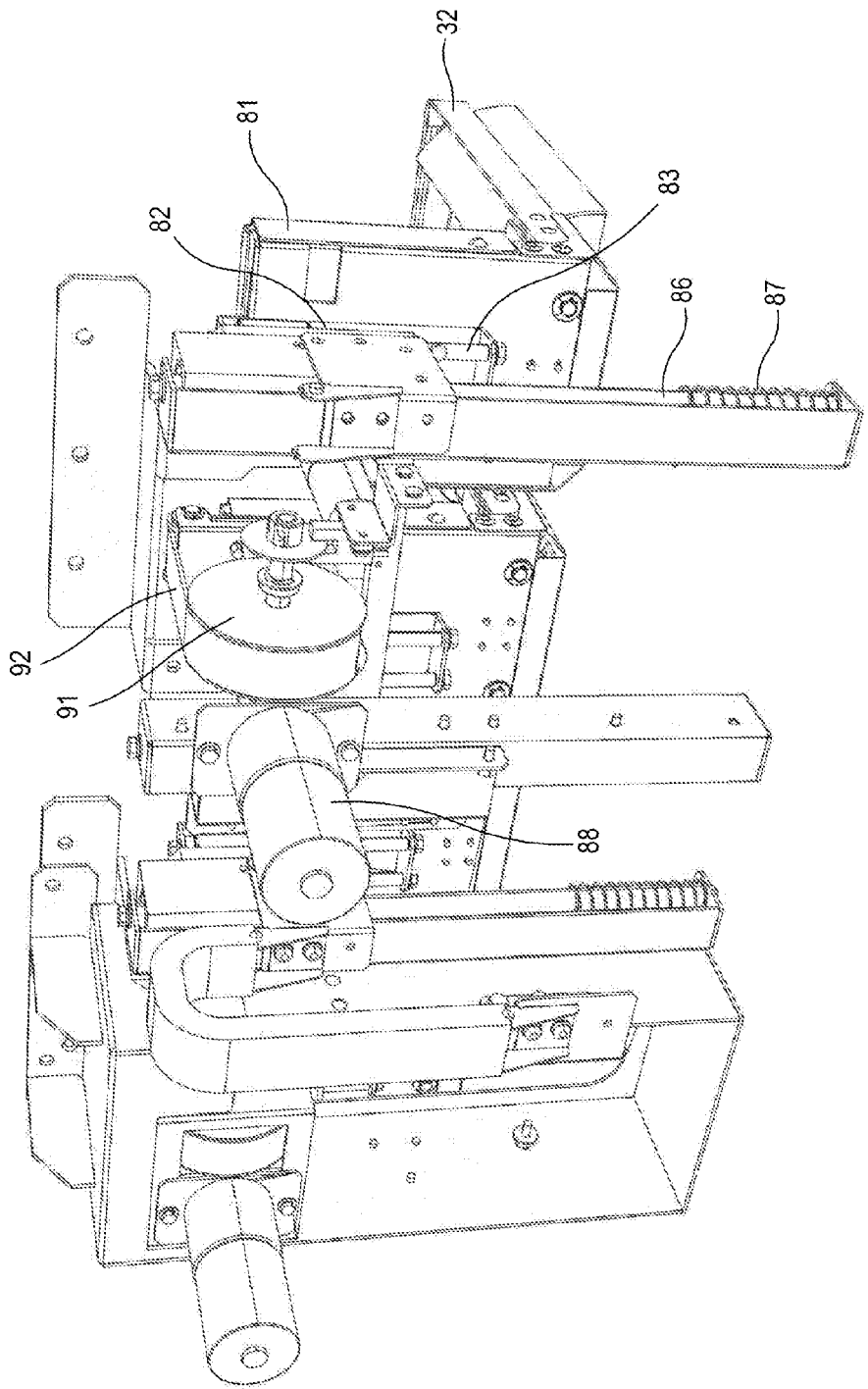
FIG. 23 is a rear perspective view of FIG. 22.
Figure 24:
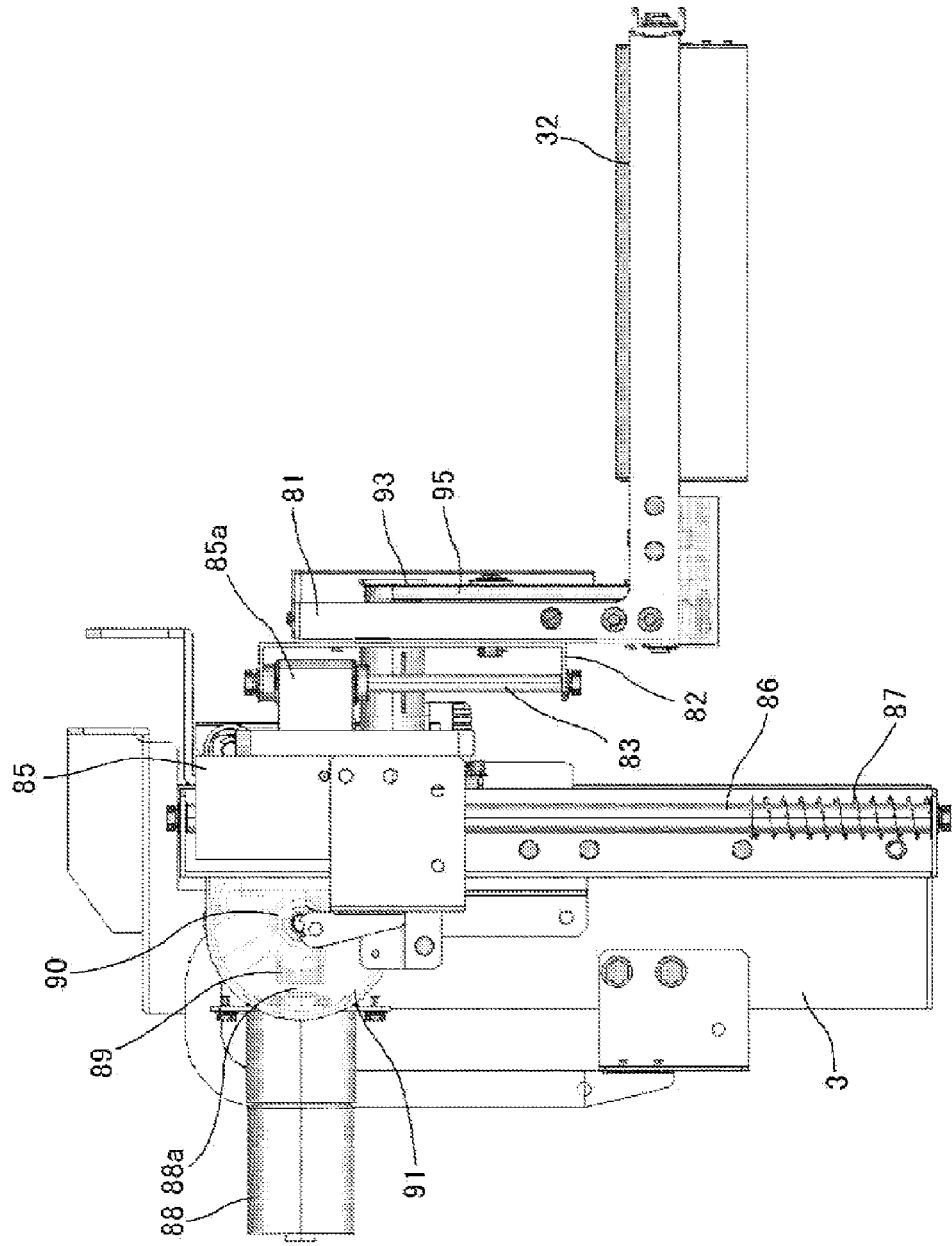
FIG. 24 is a side view of FIG. 22.

In the configuration shown in FIGS. 22 to 24, the medicine storing members 32 are configured such that two right-hand ones and two left-hand ones can be lifted or lowered together and the two right-hand ones and the two left-hand ones can be lifted or lowered apart.

Each of the medicine storing members 32 includes a back portion 81 extending upwardly in the back thereof. Guide pieces 82 of generally U-shaped cross section are anchored to back sides of the back portions respectively. Two guide shafts 83 extending vertically are juxtaposed and coupled to an upper portion and a lower portion of the guide piece 82 respectively. The two guide shafts 83 provided in the back portions 81 of the two right-hand medicine storing members 32 pass through two supporters 84a provided in front of a first support block 84. Also, the two guide shafts 83 provided in the back portions of the two left-hand medicine storing members 32 pass through two supporters 85a provided in front of a second support block 85. Thus, the back portions 81 (i.e., the medicine storing members 32) can be lifted and lowered independently with respect to the support blocks 84, 85 through the guide shafts 83.

The support blocks 84, 85 are supported by slide shafts 86 provided in the device body 3 so as to be lifted and lowered. Coil springs 87 encircle the slide shafts 86 respectively. When the support block 84, 85 is lowered, the coil spring 87 resiliently supports the support block, thus preventing the medicine storing member 32 from colliding against the medicine collecting container 34. The coil springs 87 may be directly attached to respective support blocks 84, 85 (the coil spring does not necessarily to encircle the slide shaft 86.).

Normal and reverse operation of a motor 88 performs lifting and lowering of the support blocks 84, 85 and the medicine storing members 32, via a drive gear 89, a driven gear 90, a pulley 91 and a belt 92. Specifically, the drive gear 89 is integrated with a rotating shaft 88a of the motor 88 and the driven gear 90 is in mesh with the drive gear 89. The pulley 91 is integrated with the driven gear 90. Further, one end of the belt 92 is fixed to the pulley 91. As the pulley 91 is normally or reversely rotated, the belt 92 can wind up or wind down. The opposite end of the belt 92 is connected to the support block 84, 85 supporting the two medicine storing members 32. Thus, as the motor 88 is normally and reversely operated, the support blocks 84, 85 and the medicine storing members 32 are lifted and lowered via the gears 89, 90, the pulley 91 and the belt 92.

Pulleys 93, 94 disposed up and down and a belt 95 wound therebetween are equipped in the back portion 81 of each of the medicine storing members 32. A gear 96a is integrated with a rotating shaft 94a of the lower pulley 94. In addition to the aforesaid gear 96a, three gears 96b, 96c, 96d are arranged side by side in one end of the medicine storing member 32 (total four gears). These gears 96a to 96d are disposed such that neighboring gears are in mesh with each other. Rotating shafts of the gears 96a, 96d located at either end serve as rotation centers of a first bottom plate 97 and a second bottom plate 98. Thus, as the motor 88 is normally and reversely operated, the first bottom plate 97 and the second bottom plate 98 are synchronously rotated via the gears 96a to 96d, thus opening and closing a bottom side of the medicine storing member 32.

Similar to the foregoing embodiment, medicines are supplied from the medicine receiving container 19 or the orientation changing container 61 to the medicine storing member 32 configured as described above. When medicines are supplied, the motor 88 is operated to lift the support blocks 84, 85 along the slide shaft 86, thus positioning the medicine storing members 32 to an upper receipt position.

When each of the medicine storing sections 37 receives the medicines, the medicine collecting container 34 is appropriately positioned below the medicine storing member 32. Then, the motor 88 is reversely operated to position the medicine storing member 32 to a lower delivery position. In this case, as the medicine storing member 32 is lowered up to a predetermined position, the support block 84, 85 is brought into abutment with the coil spring 87. Then, the upward bias force acts on the support block to weaken its lowering speed, thereby preventing the problem that the medicine storing member 32 collides against the medicine collecting container 34 and one or both of them are damaged thereby.

If the medicine collecting container 34 is positioned to the delivery position as described above, then the bottom plates 97, 98 are opened to discharge the medicines to each of the medicine collecting sections 44 of the medicine collecting container 34. In this regard, even if the medicines received in the medicine collecting container 34 interfere with the opened bottom plates 97, 98, the bottom plates are moved upwardly and thus excessive load is not applied to the medicines, since the coil spring 87 provides for the resilient support and each of the medicine storing sections 37 is slidably supported by the guide shaft 83.

According to the foregoing embodiments, the ampoules 12 are ejected from the cassettes 9 in the transverse orientation. However, the ampoules 12 may be ejected in the longitudinal orientation.

Figure 25:
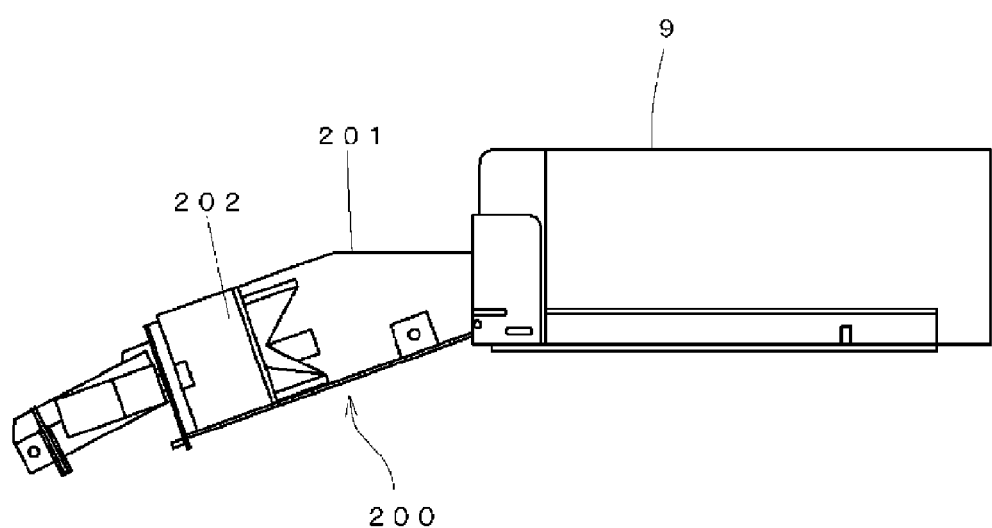
FIG. 25 is a side view of a dispensing member, showing a mechanism dispensing medicines from a medicine container in accordance with another embodiment.

Specifically, as shown in FIG. 25, the ampoules 12, which are randomly contained in the cassettes 9, are ejected in the longitudinal orientation (in a length direction) by a dispensing member 200. The dispensing member 200 includes a guide passage 201 and a rotor 202 rotatably disposed in the guide passage. The rotor has a generally cylindrical shape and includes a plurality of holding recesses (not shown) at an outer periphery in an axial direction. As the rotor 202 rotates, the ampoules 12 longitudinally held in the holding recesses are ejected from the guide passage 201 one at a time.

Figure 26:
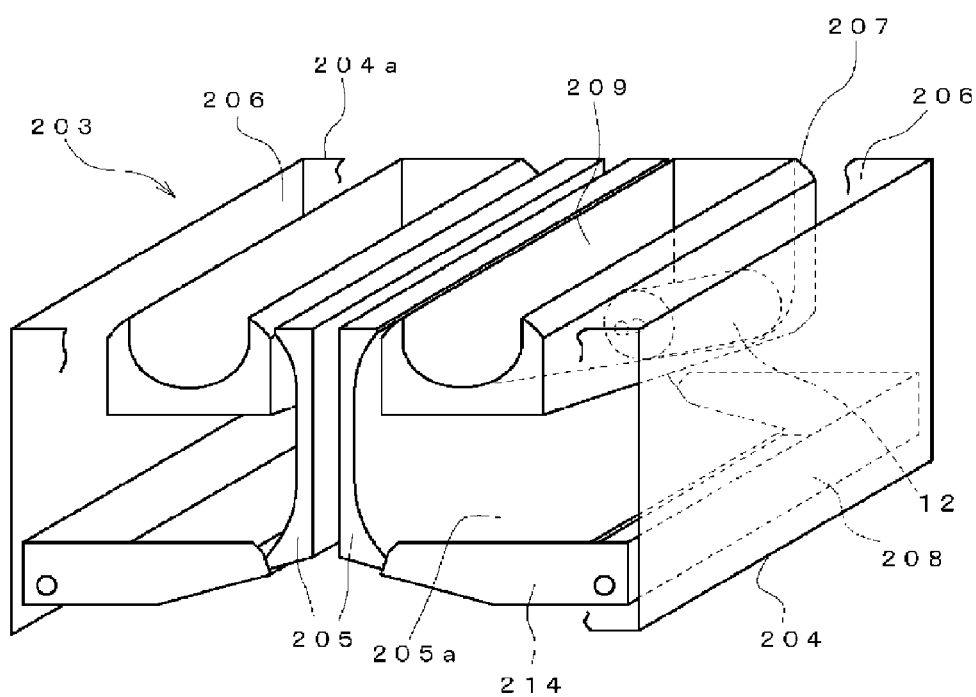
FIG. 26 is a diagrammatical perspective view showing a medicine receiving unit in accordance with another embodiment.

A medicine receiving unit 203 shown in FIG. 26 receives the ampoule 12 ejected from the cassette 9. The medicine receiving unit 203 is constructed such that a pair of partition plates 25 bisect the interior of a frame body 205 to define two juxtaposed receiving sections 206. A movement range of the medicine receiving unit is set such that the receiving sections 206 are only within a frontal area (where the medicines are ejected) of an occupancy space of the cassettes 9 arranged in array and do not protrude laterally beyond the frontal area. This provides for compact construction of the entire device.

Characteristic operations of the medicine receiving unit 203 will be described in greater detail.

Figure 29:
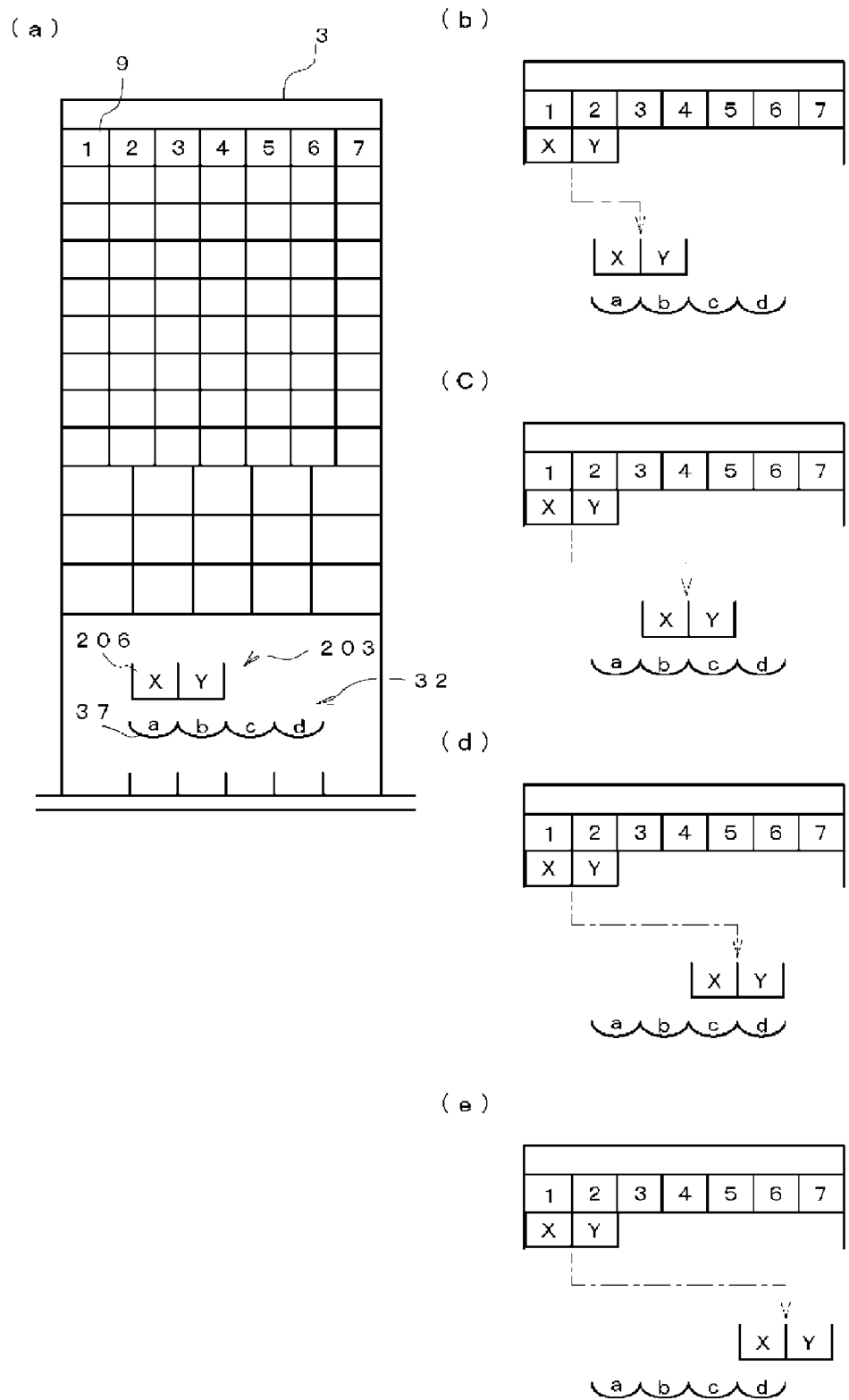
FIG. 29 illustrates operations of dispensing medicines from the medicine containers in left-hand columns using the medicine receiving unit shown in FIG. 26.

As to leftmost and rightmost (vertical) columns in the cassettes 9 that are arranged upwardly, downwardly leftward and rightward, only one of the receiving sections 206 can receive the dispensed medicines due to the above-mentioned restriction in the movement range of the medicine receiving unit 203. For example, as shown in FIG. 29(a), when the cassettes 9 of a number one to a number seven are mounted in the uppermost row and each of the receiving sections 206 of the medicine receiving unit 203 receives the medicines from the cassette 9 of number one, only the receiving section 206 in an X position can do. In this case, in order to dispense the medicine contained in the cassette 9 of number one to each of the medicine storing sections 37 (a to d) of the medicine storing member 32, the medicine receiving unit 203 needs to be moved as shown in FIGS. 29(b) to 29(e). On the contrary, as shown in FIG. 30(a), when dispensing the medicines from the cassette 9 of number seven, only the receiving section 206 in a Y position can receive the medicine. In this case, the medicine receiving unit 203 needs to be moved as shown in FIGS. 30(b) to 30(e).

Medicines that are used with a low usage frequency may be contained in the cassettes 9 located in the leftmost and rightmost columns. This can diminish occasions of medicine receipt using only one of the receiving sections 206 and further can achieve reduction in medicine dispensing time. In this regard, the low usage frequency may be determined based on a prescription frequency included in past prescription data (e.g., the number of medicines to be prescribed).

Each of the receiving sections 206 includes a receiving rotator 207 and a bottom plate 208, which are pivotally attached to the frame body 204. Curved surfaces 205*a* gradually projecting inwardly are formed up and down in each of the partition plates 205.

The receiving rotator 207 is formed by molding from a synthetic resin material and includes a receiving groove portion 209 of general U-shaped cross section. The receiving rotator is supported on one side by a frontal plate 204*a* of the frame body 204 to be pivotal about a spindle 207*a*. The receiving groove portion 209 is configured to be open upwardly and toward the cassette 9 in a normal position shown in FIG. 27(1) and to be gradually inclined downwardly (become deeper) from the cassette 9 toward the front. An opening (having a semi circular shape) of the receiving groove portion 209 facing toward the cassette 9 is positioned to a dispensing opening of the dispensing member 200. Further, an inclination angle of the receiving groove portion 209 is set to allow for smooth movement of the medicine dispensed from the cassette 9 and not to cause too fast movement. In this embodiment, the inclination angle is set to about 20 degrees. However, such an angle may change depending upon difference in slide of the ampoules 12 resulting from a factor such as the material of the receiving rotator 207, a surface roughness of the receiving groove portion 209, etc.

Figure 28:
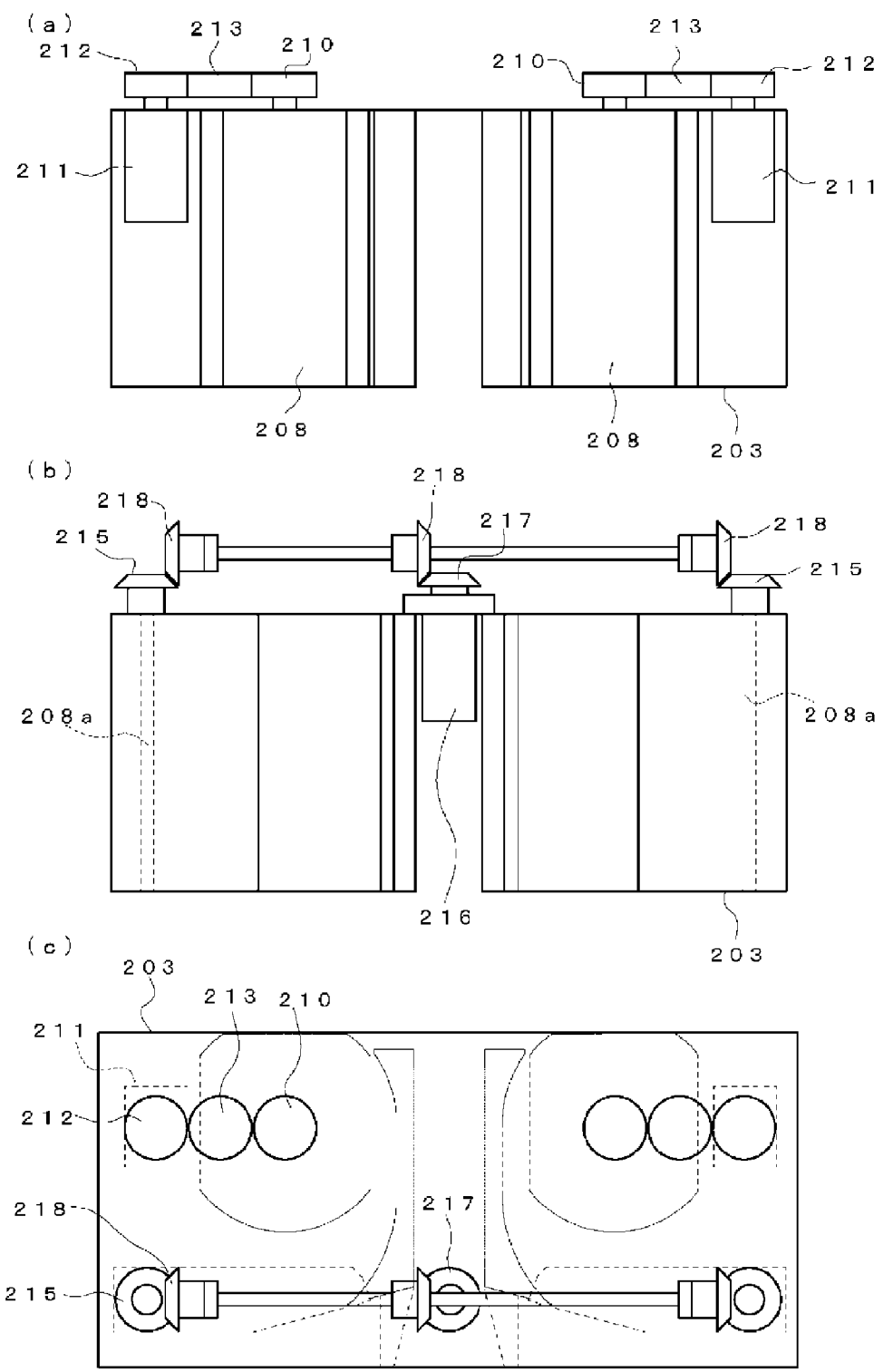
FIGS. 28(a), 28(b) and 28(c) are a plan view, a bottom view and a rear view of the medicine receiving unit shown in FIG. 26 respectively.

As shown in FIGS. 28(*a*) and 28(*c*), a driven gear 210 is integrated with the spindle 207*a* of the receiving rotator 207. A power from a motor 211 is transmitted to the driven gear 210 via a drive gear 212 and an intermediate gear 213 to rotate the receiving rotator 207. A rotating direction of the receiving rotator 207 is a direction wherein the receiving rotator 209 is directed from the partition plate 205 to the bottom plate 208.

As shown in FIG. 26, a portion of a bottom of the receiving rotator 207 includes an inclined surface that is gradually inclined toward the front in conformity with the inclination of the receiving groove portion 209. Further, the receiving rotator 207 has tapered surfaces in both lateral edge portions of the receiving groove portion 209 to avoid interference with the partition plate 205 during its rotation. Further, the receiving rotator 207 includes a through aperture (not shown) that opens above the receiving groove portion 209. The ampoules 12 being passing can be detected by an optical sensor (that includes a light-emitting element and a light-receiving element) by means of such a through aperture. Accordingly, for example, in the event that the ampoules 12 are dispensed from the cassette 9 but cannot be detected by a sensor, it is possible to detect a trouble such as halfway jamming caused by the ampoules 12. Further, preferably, an elastic member (not shown) such as urethane rubber is adhered to an inner end surface of the receiving groove portion 209 of the receiving rotator 207 as a buffer means. Thus, even if the ampoule 12 (in particular, its head portion) sliding on the receiving groove portion 209 collides against the inner end surface, damages are not caused to the ampoule. Further, instead of the elastic member, a deceleration section (e.g., a horizontal surface or a curved surface) for slowing down the movement speed of the ampoule 12 may be provided in a terminal position in inclination when the receiving rotator 207 is in the normal position. In such a case, the deceleration section becomes the buffer means.

Further, preferably, a shock absorbing member (e.g., urethane) is adhered to a front inner surface of the receiving groove portion 209. Accordingly, even if the ampoule 12 slides on the receiving groove portion 209 and collides against the inner surface in one end, a shock therefrom can be sufficiently buffered.

Figure 27:
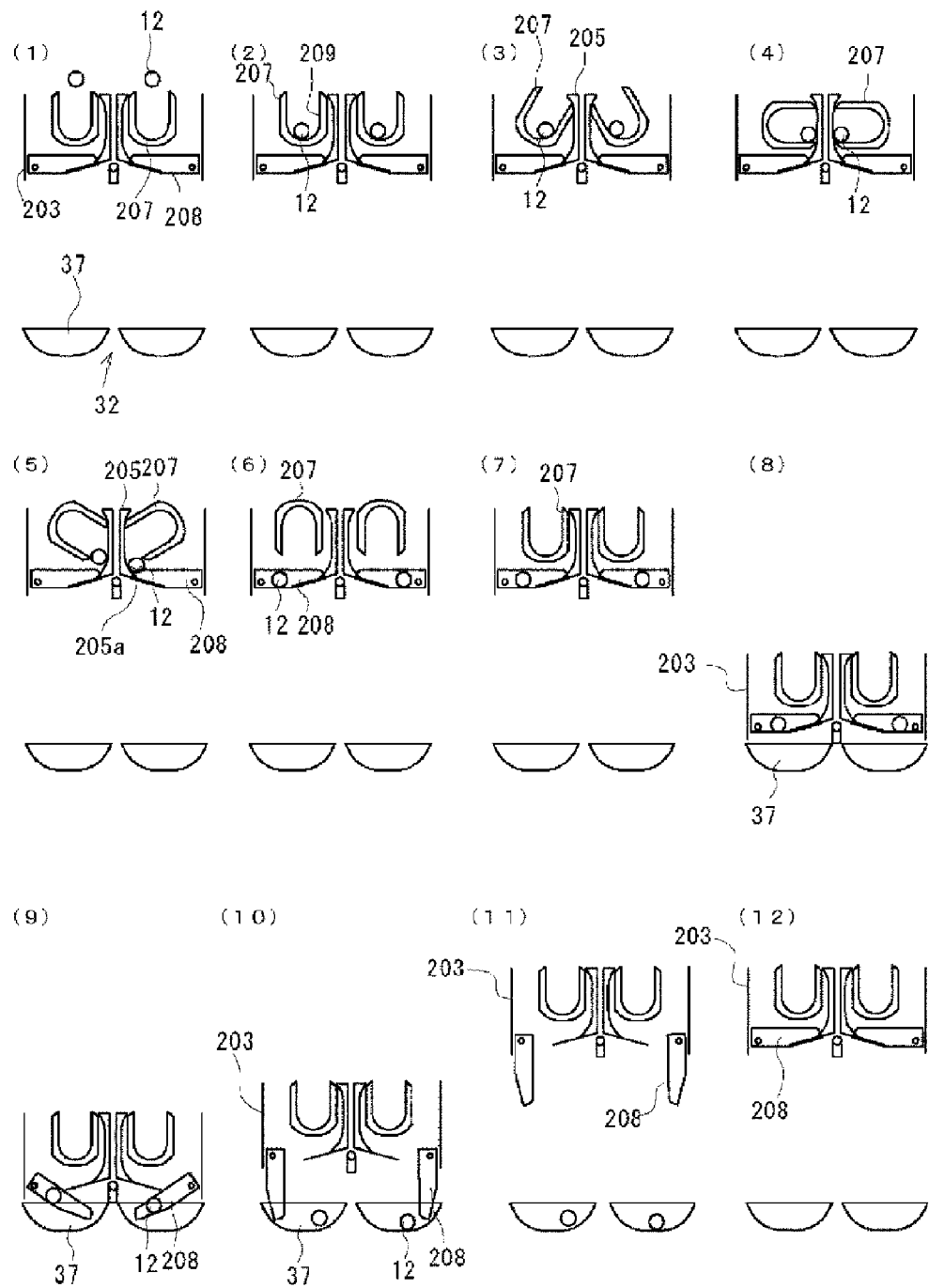
FIG. 27 illustrates operations of dispensing medicines to the medicine storing member using the medicine receiving unit shown in FIG. 26.

As shown in FIG. 27, the bottom plate 208 is provided in the frame body 204 to be pivotal about a spindle 208*a* between a closed position and an opened position. As shown in FIGS. 28(*b*) and 28(*c*), a driven gear 215 is integrated with the spindle 208*a* and a drive power from a motor 216 is transmitted to the driven gear via a drive gear 217 and a driven gear 218. Further, when the motor 216 is de-energized, the bottom plate 208 is pivotable. Guide walls 214, which extend from both sides and edges adjacent to the spindle of the bottom plate, are formed in the bottom plate 208. Further, a leading end portion (opposite the spindle 208*a*) of the bottom plate 208 is formed to be gradually upwardly inclined toward the leading end. When in the closed position, the bottom plate 208 is in abutment with a lower surface of the lower end portion (horizontally projecting portion) of the partition plate 205, thereby forming a retention area capable of retaining the ampoule 12 by means of the partition plate 205, the guide wall and a portion of a bottom surface.

The medicine dispensing device including the aforesaid members dispenses the ampoules 12 as follows.

Specifically, if the cassette 9 containing the corresponding ampoule 12 is specified based on a prescription data, then the medicine receiving unit 203 is moved up to the front of such a cassette 9. Subsequently, the opening portion of the receiving rotator 207 of the medicine receiving unit 203 is positioned to the dispensing opening of the dispensing member 200. At this state, as the rotor 202 of the dispensing member 200 is rotated, the ampoules 12 are dispensed from the cassette 9 one at a time (FIG. 27(1)). The dispensed ampoule 12 enters into the receiving groove portion 209 of the receiving rotator 207 of the medicine receiving unit 203 in the longitudinal orientation (FIG. 27(2)).

The receiving groove portion 209 is formed to be gradually downwardly inclined along the dispensing direction of the ampoule 12, as described above. Moreover, its inclination angle is set appropriately. Accordingly, the ampoule 12 dispensed from the cassette 9 in the longitudinal orientation smoothly moves on the receiving groove portion 209 without being subjected to impact and then stops with the leading end portion in abutment with the inner surface.

If delivering the ampoule 12 to the receiving rotator 207 is finished, the motor 211 is operated to rotate the receiving rotator 207 (FIG. 27(3)). As the receiving rotator 207 is rotated, the ampoule 12 retained in the receiving groove portion 209 rolls on the inner surface of the receiving groove portion from the deepest position to the one side edge (FIG. 27(4)). Subsequently, as the side edge is away from the curved surface 205*a* of the lower end of the partition plate 205 (FIG. 27(5)), the ampoule, in turn, rolls on the curved surface 205*a* and then reaches the bottom plate 208 (FIG. 27(6)). Thereafter, the receiving rotator 27 returns to the normal position and then dispensing the next ampoule 12 is performed (FIG. 27(7)).

If the ampoules 12 are dispensed from the cassette 9 by the predetermined number included in the prescription data, similar to the foregoing, then the medicine receiving unit 203 is moved to the medicine storing member 32 of the medicine collecting unit (FIG. 27(8)). Subsequently, the bottom plates 208 are pivoted by operation of the motor to open the bottom side (FIG. 27(9)) and thus the ampoules 12 retained on the bottom plates 108 are discharged to each medicine storing section 37 of the medicine storing member 32. Further, the medicine receiving unit 203 is gradually moved upwardly in concomitance with pivoting of the bottom plates 208 (FIG. 27(10)). At this time, the motor 216 is de-energized and thus the bottom plates 208 become pivotable. Accordingly, even if the ampoule 12 is sandwiched between the bottom plate 208 and the medicine storing section 37, only the weight of the bottom plate 208 acts, thereby causing no damages. As such, the ampoule 12 is smoothly discharged to the medicine storing section 37. Thereafter, the medicine receiving unit 203 is moved away from the medicine storing sections 37 with the bottom plates 208 fully opened (FIG. 27(11)) and, if sufficiently apart from the medicine collecting unit, the bottom plates 208 are pivoted to the closed position (FIG. 27(12)).

As such, the medicine dispensing device including the medicine receiving unit 203 constructed as described above can smoothly convey the ampoule 12 to the medicine collecting unit without any damage even if the ampoule is dispensed in the longitudinal orientation. In particular, since the ampoules 12 can be transferred one by one to the bottom plates 208 through the receiving rotator 207, the ampoules do not interfere with one another. And, it is possible to prevent the problem that the head portion prone to damage may break off. Further, the ampoules are arranged longitudinally side by side on the bottom plate 208. Accordingly, the ampoule 12 rolling down due to the rotation of the receiving rotator 207 and the ampoule 12 previously existing on the bottom plate 208 do not sustain damages even if they collide against each other.

The receiving rotator 207 includes the receiving groove portion 209 of general U-shaped cross section, but may be configured otherwise. For example, the receiving rotator may be configured in a generally cylindrical shape and have an opening permitting the ampoule 12 to pass therethrough at a portion of an outer periphery thereof. In such a case, the receiving rotator 207 may be rotated with the ampoule 12 retained therein, so that when the opening is moved downwardly, the ampoule 12 can be moved to the curved surface 205a in the lower end of the partition plate 205.

The invention claimed is:

1. A medicine dispensing device, comprising:
    a device body;
    a medicine containing unit mounted in the device body, the medicine containing unit including a plurality of medicine containers each configured to dispense medicines contained therein through a corresponding medicine ejecting portion;
    a medicine receiving unit movably provided in the device body, the medicine receiving unit having at least two medicine receiving sections that are movable to each of the medicine containers of the medicine containing unit to receive the medicines dispensed from the medicine ejecting portion and are movable to a discharging position to discharge the received medicines;
    a medicine collecting unit having a plurality of medicine collecting sections, each of the medicine collecting sections configured to collect the medicines discharged from each of the medicine receiving sections in the discharging position;
    a control unit configured to move each of the medicine receiving sections based on a prescription data such that the medicine receiving sections receive the medicines dispensed from the medicine container and discharge the medicines to the corresponding medicine collecting section of the medicine collecting unit; and
    a medicine storing member having a plurality of medicine storing sections, each of the medicine storing sections temporarily storing the medicine received in each of the medicine receiving sections of the medicine receiving unit before the medicine received in each of the medicine receiving sections is discharged to each of the medicine collecting sections.

2. The medicine dispensing device of claim 1, wherein the medicine containing unit is configured to arrange the medicine ejecting portions along any reference plane in the device body, and
    wherein the medicine receiving unit includes a supporting member supporting the medicine receiving sections such that each of the medicine receiving sections is movable upward, downward, leftward, and rightward along the reference plane.

3. The medicine dispensing device of claim 1, wherein the medicine receiving unit includes a medicine receiving container comprising two medicine receiving sections arranged horizontally side by side, and
    wherein the medicine receiving container is reciprocably movable such that each of the medicine receiving sections are movable to receive medicines dispensed from the medicine ejecting portions.

4. The medicine dispensing device of claim 1, wherein the medicine receiving unit includes four medicine receiving sections arranged horizontally side by side, and
    wherein the medicine receiving sections located at either end are upwardly or downwardly movable with respect to the centrally located medicine receiving sections and further are movable toward one another after being moved upwardly or downwardly to align with respect thereto.

5. The medicine dispensing device of claim 1, wherein the medicine receiving unit includes two medicine receiving containers each comprising two medicine receiving sections arranged horizontally side by side, and
    wherein each of the medicine receiving sections of each of the medicine receiving containers is movable in upward, downward, leftward, and rightward relative directions.

6. The medicine dispensing device of claim 1, wherein the medicine is longitudinally elongated,
    wherein the medicine collecting unit is configured such that the medicine collecting sections are longitudinally elongated and are arranged side by side in a direction orthogonal to a longitudinal direction thereof, and
    wherein the medicine dispensing device further comprises at least one orientation changer located between the medicine receiving unit and the medicine collecting unit, the orientation changer being pivotable between a receipt position at which the changer receives the medicine from the medicine receiving section of the medicine receiving unit and a delivery position at which a longitudinal direction of the medicine is in accord with the longitudinal direction of the medicine collecting section.

7. The medicine dispensing device of claim 6, wherein a first orientation changer begins to pivot from the receipt position to the delivery position and thereafter a second orientation changer begins to pivot from the receipt position to the delivery position.

8. The medicine dispensing device of claim 1, wherein the plurality of the medicine storing sections of the medicine storing member are configured to be lifted and lowered integrally and each of the medicine storing sections is supported so as to be lifted and lowered independently.

9. The medicine dispensing device of claim 1, wherein the medicine comprises a plurality of ampoules each having a longitudinal direction, wherein the medicine containing unit includes a dispensing member dispensing the ampoules one at a time in the longitudinal direction, and wherein the medicine receiving unit includes:
- a receiving rotator supporting the dispensed ampoules and transferring the supported ampoules downwardly through rotation; and
- a bottom plate supporting the transferred ampoules downwardly through the rotation of the receiving rotator and pivoting to discharge the ampoules downwardly.

10. The medicine dispensing device of claim 9, wherein the receiving rotator includes a receiving groove portion having a U-shaped cross section,
   wherein the receiving groove portion is formed to be gradually downwardly inclined toward a direction in which the ampoules are ejected from the medicine container when the receiving rotator is in a normal position, and
   wherein the receiving groove portion includes a buffer means buffering an impact exerted to the transferred ampoules.

11. The medicine dispensing device of claim 10, wherein the receiving rotator is rotatably supported on one side opposite the medicine container and the receiving groove portion opens toward an end surface of the medicine container in the normal position.

12. The medicine dispensing device of claim 10, wherein the medicine receiving unit includes a partition plate disposed along a rotation direction of the receiving rotator and configured to guide the ampoule supported by the receiving groove portion until the ampoule is discharged to the bottom plate.

13. The medicine dispensing device of claim 9, wherein the medicine receiving unit includes a plurality of receiving sections arranged horizontally side by side, and
   wherein the medicine receiving unit is configured to be movable within a range wherein the medicine receiving unit does not protrude leftward and rightward with respect to the medicine containers arranged upwardly, downwardly, leftward, and rightward.

14. The medicine dispensing device of claim 1, wherein the medicine receiving unit includes a plurality of receiving sections arranged horizontally side by side, and
   wherein the medicine receiving unit is configured to be movable within a range wherein the medicine receiving unit does not protrude leftward and rightward with respect to the medicine containers arranged upwardly, downwardly, leftward, and rightward.

* * * * *